(12) United States Patent
Gutmann et al.

(10) Patent No.: US 8,221,731 B2
(45) Date of Patent: Jul. 17, 2012

(54) CONTINUOUS MOISTURIZATION COMPOSITIONS

(75) Inventors: Erik Gutmann, Minneapolis, MN (US); Peter Matravers, San Gabriel, CA (US); Barbara Jean Fealy, Fridley, CA (US); Nathan Keen, Anoka, MN (US)

(73) Assignee: Aveda Corporation, Blaine, MN (US)

( * ) Notice: Subject to any disclaimer, the term of this patent is extended or adjusted under 35 U.S.C. 154(b) by 347 days.

(21) Appl. No.: 12/467,450

(22) Filed: May 18, 2009

(65) Prior Publication Data

US 2009/0297466 A1 Dec. 3, 2009

Related U.S. Application Data

(60) Provisional application No. 61/057,243, filed on May 30, 2008.

(51) Int. Cl.
*A61K 5/12* (2006.01)
*A61K 8/02* (2006.01)

(52) U.S. Cl. .............................. 424/70.12; 424/401

(58) Field of Classification Search ............. 424/70.12, 424/401
See application file for complete search history.

(56) References Cited

U.S. PATENT DOCUMENTS

| | | |
|---|---|---|
| 3,439,088 A | 4/1969 | Edman |
| 3,818,105 A | 6/1974 | Coopersmith et al. |
| 4,240,450 A | 12/1980 | Grollier et al. |
| 5,573,709 A | 11/1996 | Wells |
| 5,716,418 A | 2/1998 | Matzik et al. |
| 5,756,079 A | 5/1998 | Cauwet et al. |
| 5,843,193 A | 12/1998 | Hawkins et al. |
| 6,648,026 B2 | 11/2003 | Look et al. |
| 6,695,510 B1 | 2/2004 | Look et al. |
| 6,955,489 B2 | 10/2005 | Look et al. |
| 7,073,965 B2 | 7/2006 | Look et al. |
| 2005/0196372 A1 | 9/2005 | Cajan et al. |
| 2005/0198747 A1* | 9/2005 | Emmerling et al. ............... 8/406 |
| 2006/0018867 A1 | 1/2006 | Kawasaki et al. |
| 2006/0165636 A1 | 7/2006 | Hasebe et al. |
| 2006/0188315 A1 | 8/2006 | Look et al. |
| 2006/0251602 A1 | 11/2006 | Goddinger et al. |
| 2008/0120791 A1 | 5/2008 | Hoffmann et al. |

FOREIGN PATENT DOCUMENTS

| | | |
|---|---|---|
| BR | PI0303404-6 | 8/2005 |
| EP | 1602354 | 12/2005 |
| EP | 1604647 | 12/2005 |
| JP | 2000319120 | 11/2000 |
| WO | WO 98/48768 | 11/1998 |
| WO | WO 98/50005 | 11/1998 |
| WO | WO 01/91605 | 12/2001 |
| WO | WO 2004/084646 | 10/2004 |
| WO | WO 2006/120646 | 11/2006 |

OTHER PUBLICATIONS

Kaufman, M.; Wiesman, Z. Pomegranate Oil Analysis with Emphasis on MALDI-TOF/MS Triacylglycerol Fingerprinting. J. Agric. Food Chem. 2007, 55, 10405-10413.*

Drovetskaya, et al.; Effects of Low Level Hydrophobic Substitution on Conditioning Properties of Cationic Cellulosic Polymers in Shampoo Systems; DOW; Presentation at the Conference on Applied Hair Science; pp. 1-6; Jun. 2004.

PCT International Search Report; International Application No. PCT/US2009/044621, Completion Date: Jan. 5, 2010; Date of Mailing: Jan. 7, 2010.

PCT Written Opinion of the International Searching Authority, or the Declaration; International Application No. PCT/US2009/044621; Completion Date: Jan. 5, 2010; Mailing Date: Jan. 7, 2010.

* cited by examiner

*Primary Examiner* — Fereydoun G Sajjadi
*Assistant Examiner* — Genevieve S Alley
(74) *Attorney, Agent, or Firm* — Cynthia R. Miller

(57) ABSTRACT

An aqueous hair moisturizing composition is provided. The composition includes a cationic component, an oil containing about 70 percent or greater unsaturated fatty acids with chain length of $C_{18}$ or greater, a phytosterol and a cellulosic polymer. Also provided is a method of imparting extended moisturization to the hair including the steps of applying to the hair in need of extended moisturization a composition including a cationic component, an oil containing about 70 percent or greater unsaturated fatty acids with chain length of $C_{18}$ or greater, a phytosterol and a cellulosic polymer, and retaining the composition in contact with the hair for a time sufficient to impart extended moisturization to the hair.

26 Claims, 1 Drawing Sheet

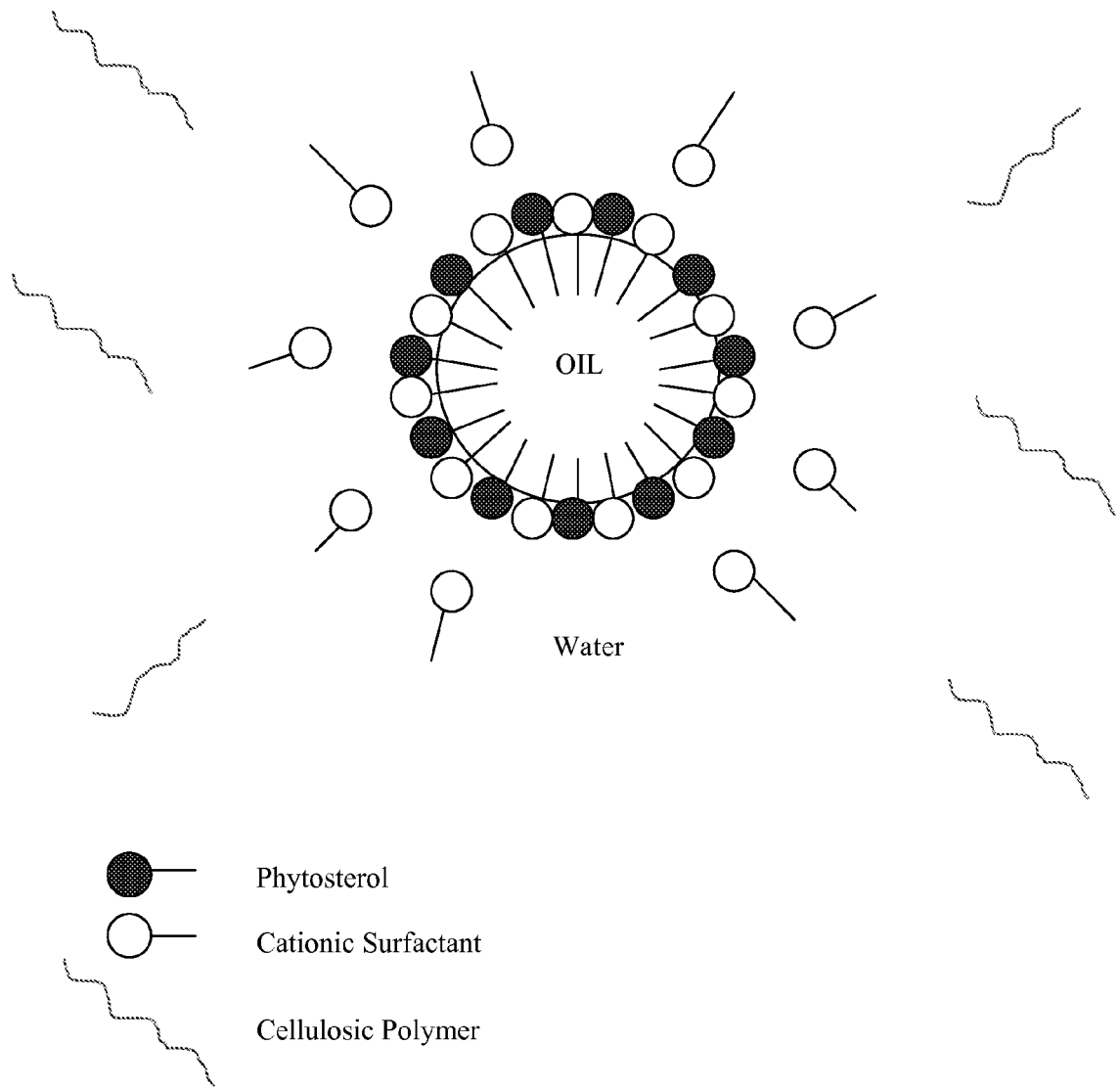

CONTINUOUS MOISTURIZATION COMPOSITIONS

CROSS REFERENCE TO RELATED APPLICATIONS

This application claims priority of U.S. Provisional Patent Application Ser. No. 61/057,243 filed on May 30, 2008.

FIELD OF THE INVENTION

The present invention relates to personal care products. In particular, the present invention is concerned with products employed to condition the hair, the scalp and the skin.

BACKGROUND OF THE INVENTION

The buildup of sebum in the hair together with soil attracted to the hair from the surrounding atmosphere causes the hair to have an unattractive appearance. Shampooing the hair removes the dirt and sebum; however, frequent shampooing can leave the hair tangled and therefore difficult to comb. Additional undesirable effects of frequent shampooing include dry hair and/or scalp. This can prove particularly problematic for color treated, bleached, permed and/or otherwise damaged hair. To solve these problems a wide variety of products has been developed for use in conditioning the hair, including moisturizing components in shampoos and post-shampoo hair conditioners. There is of course a large number of different hair conditioning products currently on the market providing adequate initial conditioning to the hair. Heretofore, however, it has been difficult in the field to provide long lasting moisturization to the hair, and to do so without leaving the hair with a greasy look or feel.

The present invention meets the demand for hair conditioning products which achieve long lasting moisturization whether delivered through a cleansing or a conditioning system. Unexpectedly, the shampoos developed according to the present invention effectively cleanse the hair while providing copious foam and moisturization throughout the process. Moreover, the products of the invention also meet the consumer demand for products utilizing plant-based ingredients.

A common method of providing a conditioning benefit has been the use of cationic surfactants such as cellulose derivatives, for example, cationic quaternary ammonium compounds, such as polyquaternium compounds, for example, Polyquaternium-10, which form polymer-surfactant complexes or coacervates with surfactants, which precipitate on hair, making it softer, smoother and easier to comb. Cationic surfactants are those in which the surfactant activity resides in the positively charged cation portion of the molecule. The cationic surfactants are therefore attracted to the negatively charged hair surface and, because of their relatively low solubility and high molecular weight, are thermodynamically driven to leave the aqueous environment of the shampoo and deposit on the hair. These characteristics make cationic surfactants such as quaternary ammonium compounds particularly suited to the treatment of human hair. Thus, many hair conditioning products are based on quaternary ammonium compounds. The inventors have surprisingly discovered, however, that the cationic ingredients in the compositions of the present invention act as carriers in aqueous systems optimizing the other components to deliver attributes through superior enhanced moisturization which effect a moisturized feel, softness, brilliance, suppleness and smooth combing of the hair, both wet and dry. It is contemplated that the present invention may be used in cleansing, conditioning and treatment products for the scalp, hair and body.

SUMMARY OF THE INVENTION

The present invention describes an aqueous moisturizing treatment for the hair, scalp or skin, comprising:
 a. a cationic compound
 b. an oil containing about 70% or greater unsaturated fatty acids of chain length $C_{18}$ or greater;
 c. a phytosterol; and
 d. a cellulosic polymer.

Preferably a, b, c and d are present in a ratio of about 0.5-1:0.7-1.5:0.7-1.5:1-2, preferably in a ratio of about 0.8:1:1:1.5, based on the total weight of the composition.

The present invention also describes a method of providing long-term moisturization to the hair, scalp or skin, comprising the step(s) of:
(1) contacting the hair, scalp or skin with an aqueous composition comprising:
 a. a cationic compound
 b. an oil containing about 70% or greater unsaturated fatty acids of chain length $C_{18}$ or greater;
 c. a phytosterol; and
 d. a cellulosic polymer; and
(2) retaining the composition in contact with the hair, scalp or skin for a time sufficient to moisturize the hair, scalp or skin. Preferably a, b, c and d are present in a ratio of about 0.5-1:0.7-1.5:0.7-1.5:1-2, preferably in a ratio of about 0.8:1:1:1.5, based on the total weight of the composition.

Typically, each of the four components is present in the compositions at a level in the range of from about 0.05% to about 20%, based on the total weight of the composition. In a preferred embodiment of the present invention, the compositions of the present invention are comprised of from about 0.1% to 10% of cationic quaternary ammonium compound; from about 0.25% to about 2.5% of oil; from about 0.25% to about 2.5% of sterol; and from about 0.375% to about 3.75% of cellulosic polymer.

Aqueous carriers suitable for use in the compositions of the present invention include water, such as deionized, distilled, tap, spring, floral and the like; and water solutions of alkyl alcohols, polyhydric alcohols; and preferably are used in amounts from about 20-99.8% in combination, based on the total weight of the composition.

Those skilled in the art will appreciate that the compositions of the invention may also be provided in a concentrated form, containing little or no water. For use, the concentrate would be introduced into water prior to application to the hair, scalp or skin. The concentrated formulation would have the same ratio of components as for the aqueous composition.

By use of the term "comprising", herein, it is intended that the compositions of the invention may include any other cosmetically suitable ingredients which do not adversely affect the end result to be achieved by the product; that is, superior moisturization of the hair, scalp or skin to which the composition is applied.

Additional features and advantages of the invention are set forth in the description which follows. Advantages of the invention will be realized and attained by the cosmetic hair conditioning compositions as particularly pointed out in the description and the claims.

It is to be understood that both the foregoing general description and the following detailed description are exemplary and explanatory and are intended to provide further explanation of the invention as claimed.

BRIEF DESCRIPTION OF THE FIGURES

The FIGURE is a schematic representation of the synergistic relationship among the components of the compositions of the present invention.

DETAILED DESCRIPTION OF THE INVENTION

The moisturizing treatment compositions of the present invention comprise four ingredients in addition to water.

The Cationic Component

The first ingredient in the present invention to be discussed is a cationic component. The cationic component may be in the form of a cationic compound or a cationic polymer. Preferably, the cationic component is included in the compositions of the present invention as an emulsifying agent and/or for its surfactant or conditioning properties.

The cationic compound may be a cationic quaternary compound such as an ammonium salt or salts of fatty amines or amidoamines. Suitable quaternary ammonium salts include those of the formula:

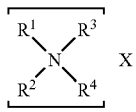

wherein R1, R2, R3, and R4 are each independently a saturated or unsaturated aliphatic group of 1 to 45 carbon atoms, or aromatic, aryl, or alkaryl group having 1 to 45 carbon atoms; and X is an anion selected from halogen (such as fluorine, chlorine, iodide, bromine, etc.) acetate, ammonia, phosphate, nitrate or methyl sulfate radicals. The aliphatic groups may contain, in addition to carbon atoms, ether linkages as well as amine or amido groups. Suitable quaternary ammonium compounds may be mono-long chain alkyl, di-long chain alkyl, tri-long chain alkyl, that is, the term "long chain" meaning longer than methyl, or where R1=1. In some cases one or more of R1, R2, R3, or R4 may comprise fatty radicals obtained from one more saturated or unsaturated fatty acids, for example, having 6 to 30 carbon atoms, including but not limited to palm oil, babassu oil, buriti oil, meadowfoam oil, canola oil, safflower oil, sesame oil, coconut oil, jojoba oil, corn oil, soybean oil, and the like.

Examples of such quaternary ammonium salts include but are not limited to behenalkonium chloride, behentrimonium chloride, behentrimonium methosulfate, behenamidopropyltrimonium methosulfate, cetalkonium chloride, cetrimonium chloride, cetrimonium methosulfate, dibehenyldimonium methosulfate, dicapryl/dicaprylyl dimonium chloride, babassuamidopropyltrimonium chloride, babassuamidopropyltrimonium methosulfate, babassuamido propyl konium chloride, palmamidopropyl trimonium chloride, palmamidopropyl trimonium methosulfate, stearalkonium chloride, stearmidopropyl trimonium chloride, distearyldimonium chloride, and so on. Most preferred is where the quaternary ammonium salt is derived from palm oil.

Also suitable are amidoamine salts, which are the condensation products of fatty acids with a polyfunctional amines, for example, those having the formula RCONH(CH$_2$)nNR$_1$R$_2$ where RCO is a fatty (C6-45 saturated or unsaturated alkyl or acyl group) such as stearoyl, behenyl, babassuoyl, palmitoyl, and R$_1$ and R$_2$ are methyl or ethyl, and n is 2 or 3. Examples of such compounds include stearamidopropyl dimethylamine, babassuamidopropyl dimethylamine, cocamidopropyl dimethylamine, and the like. Particularly preferred are amidoamines derived from palm oil.

Also suitable are cationic salts of fatty primary, secondary, or tertiary amines, wherein the substituted groups have 12 to 22 carbon atoms. Examples of such amines include dimethyl stearamine, dimethyl soyamine, stearylamine, myristylamine, tridecylamine, ethyl stearamine, and so on.

Cationic polymers may also be used as the cationic component. Examples of cationic polymers include, but are not limited to:

(a) copolymers of vinylpyrrolidone, (b) Homopolymers of dimethyldiallylammonium chloride, or copolymers of dimethyldiallylammonium chloride and acrylamide. Such compounds are sold under the tradename MERQUAT by Merck.

(c) Homopolymers or copolymers derived from acrylic or methacrylic acid, selected from monomer units acrylamide, methylacrylamide, diacetone-acrylamide, acrylamide or methacrylamide substituted on the nitrogen by lower alkyl, alkyl esters of acrylic acid and methacrylic acid, vinylpyrrolidone, or vinyl esters.

(d) cationic silicones. As used herein, the term "cationic silicone" means any silicone polymer or oligomer having a silicon backbone, including polysiloxanes, having a positive charge on the silicone structure itself.

Examples of other cationic polymers that can be used in the compositions of the invention are disclosed in U.S. Pat. Nos. 5,240,450 and 5,573,709, which are hereby incorporated by reference. The cationic component is preferably a cationic quaternary ammonium compound.

The cationic component is used in the compositions of the present invention in an amount in the range of from about 0.1% to about 5%, preferably an amount in the range of from about 0.1% to about 2% and most preferably in the amount of about 0.4%, by total weight of the composition.

The Oil Component

The second ingredient in the present invention to be discussed is oil. The oil is included in the compositions of the present invention as an emollient. Preferred oils for use in the compositions of the present invention are listed in Table 1. These oils contain about 70% or greater unsaturated fatty acids having a chain length of $C_{18}$ or greater, and include Buriti, soybean, meadowfoam, sesame, safflower, and canola (rapeseed) oils. Particularly preferred for use in the compositions of the present invention is Buriti or *Maurita flexuosa* fruit oil (available from Croda) which is derived from the nut of the Amazon region Buriti palm, and has traditionally been used as a food source and for construction and weaving. Buriti oil is the richest source oil (richer still than is carrot oil) in beta carotene and its breakdown product, vitamin A, collectively referred to as carotenoids. Carotenoids are important antioxidants which filter and absorb UV rays and neutralize free radicals in the skin, thus protecting skin against sun related damage. In skin care it has been reported to support the production of collagen and elastin. Buriti oil is an excellent source of tocopherols (Vitamin E) and oleic fatty acids and has a full profile of other essential fatty acids (EFAs) which the body cannot manufacture and which must be obtained from external sources, i.e., from foods. Surprisingly, however, the inventors have discovered that oils containing about 70% or greater unsaturated fatty acids of chain length greater than $C_{18}$ can be used in the present compositions to impart unexpectedly superior and long-term softening and moisturization of the hair.

TABLE I

UNSATURATED FATTY ACID
CONTENT OF NATURAL OILS

| OIL | % UNSATURATED FATTY ACIDS OF CHAIN LENGTH GREATER THAN $C_{18}$ |
|---|---|
| Buriti | 73-79 |
| Soybean | 80-85 |
| Meadowfoam | 92-100 |
| Canola | 74-100 |
| Sesame | 77-90 |
| Sunflower | 85-90 |

The oil component is used in the present invention in an amount in the range of from about 0.25 to about 2.5%, preferably from about 0.3 to about 1%, and most preferably in the amount of about 0.5% by total weight of the composition.

It should be appreciated that a fruit oil is not the same as a plant extract. While oils are pressed from the fruits or nuts of plants and provide a moisturizing property, extracts are typically aqueous-based and derived from roots, stems and leaves.

The Sterol Component

The third ingredient in the present invention to be discussed is the sterol component. The sterol component is included in the compositions of the present invention to provide a film forming and an emulsifying function. Plant or phytosterols are suitable for use in the compositions of the present invention. Useful plant phytosterols are steroid alcohols naturally occurring in plants, and include Campesterol, Sitosterol, Stigmasterol, and Ergosterol. The sterol component forms a part of the internal water insoluble phase of the emulsion. Particularly preferred phytosterols useful in the compositions of the present invention are sterols derived from the pomegranate (*Punica granatum*) sterols. Sterols are used in the present invention in an amount in the range of from about 0.25% to about 2.5%, preferably in the amount of about 0.3% to about 1%, and most preferably in an amount of about 0.5% by total weight of the composition.

As will be shown herein, as identified by in vitro testing, it is observed that the sterol component extends moisturization imparted to the hair, skin and scalp by compositions according to the present invention beyond that range of moisturization observed for compositions containing fruit oils and butters; that is, when the sterol is replaced by water soluble extracts, fruit oils or heavy butters, the extended moisturization does not occur.

The Cellulosic Polymer Component

The fourth ingredient in the present invention to be discussed is the cellulosic polymer component. The cellulosic polymer is present in the compositions of the invention for its film forming capability. The film forming functionality is important to wet combing and dry combing and also acts as a sealant.

Nonlimiting examples of cellulosic polymers suitable for use in the compositions of the invention include polysaccharide polymers, such as cationic cellulose derivatives. Examples of the cellulosic polymers useful in the compositions of the present invention are film forming alkyl cellulosic polymers, such as methyl cellulose, ethyl cellulose, hydroxyethyl cellulose, and hydroxypropyl methyl cellulose; film forming polymeric quaternary ammonium salts of the alkyl cellulosic polymers; film forming natural polymers derived from guar bean, locust bean, starches, carrageenan or xanthan gum, such as hydroxypropyl hydroxyl guar cellulose gum; and film forming naturally derived polymers comprising a combination of the above. Preferred cellulosic polymers are the salts of hydroxyethyl cellulose reacted with trimethyl ammonium substituted epoxide, referred to in the industry (CTFA) as Polyquaternium 10 which are available from Amerchol Corp. (Edison, N.J., USA) in their Polymer JR series of polymers with the most preferred being JR30M. Other preferred cellulosic polymers include cationic guar gum derivatives, such as guar hydroxypropyl trimonium chloride, specific examples of which include the Jaguar series (preferably Jaguar C-35) commercially available from Rhone-Poulenc Incorporated. Nonlimiting examples of suitable cellulosic polymers are described in the CTFA Cosmetic Ingredient Dictionary, $8^{th}$ edition, edited by Wenninger, Canterbery and McEwen, Jr. PhD, J.D. (The Cosmetic, Toiletry, and Fragrance Association, Inc., Washington, D.C. (2000)), which description is incorporated herein by reference. The cellulosic polymer is used in the present compositions in an amount in the range of from about 0.375% to about 3.75%, more preferably in the range of about 0.5 to about 1.5%, and most preferably in the amount of about 0.75%, based on the total weight of the composition.

Surprisingly, it has been discovered by the inventors that the aqueous compositions prepared according to the present invention provide stable, effective and versatile hair, scalp and skin treatment products which impart long-lasting moisturization to the hair, scalp or skin. Moisturization unexpectedly remains even after ten washings with conventional shampoo products. This is surprising, since the extended moisturization observed using the compositions of the present inventions is not characteristic of any one of the individual components of the compositions of the present invention. While not wishing to be bound by any particular theory, it is thought by the present inventors that the water insoluble oil and phytosterol components work synergistically to provide intense and extended moisturization when suspended by the cationic compound; that is, the cationic compound forms a film on the hair, scalp or skin which locks the other components onto the hair, scalp or skin surface creating a surprisingly long lasting moisturizing effect which is observed through up to ten washings with conventional shampoo products. Treatment of the hair, scalp or skin, using the compositions of the present invention leaves a residual layer of film on the surface of the hair, scalp or skin, creating a barrier which retains moisture. As indicated in the schematic in FIG. 1, it is believed that the hydrophilic emulsifier in the aqueous phase, i.e., the cationic compound, and the hydrophobic agents in the oil phase, form micelles. This allows the penetrating and conditioning effect. In addition, the external phase (aqueous phase) contains cellulosic polymer which aids in suspension of these ingredients while providing hair sealing benefits.

The compositions of the present invention may further comprise one or more optional components known or otherwise effective for use in hair care or personal care products, such as those which enhance stability, aesthetics and/or performance of the compositions, provided that the optional components are physically and chemically compatible with the essential component described herein, or do not otherwise unduly impair product stability, aesthetics or performance. Individual concentrations of such optional components may range from about 0.5-55%, based on the total weight of the compositions. Nonlimiting examples of optional components for use in the present compositions include perfumes; antidandruff agents; additional hair conditioning agents, such as silicones, for example, linear siloxane polymers, such as dimethicones and dimethiconol, and cyclic polysiloxanes, such as cyclopentasiloxane, cyclomethicones; plant extracts;

skin conditioning agents, such as plant-derived oils, and esters, such as caprylic acid esters; dyes, pearlescent aids, foam boosters, such as alkyl betaines; additional surfactants or emulsifiers; nonionic cosurfactants; suspending or thickening or viscosity adjusting agents, pH adjusting agents, preservatives, proteins, skin active agents, sunscreens, and antioxidants, for example, vitamins.

Suitable additional oils useful in the compositions of the present invention include silicones, esters, vegetable oils, synthetic oils, including but not limited to those set forth herein. The oils may be volatile or nonvolatile, and are preferably in the form of a pourable liquid at room temperature. The term "volatile" means that the oil has a measurable vapor pressure or a vapor pressure of at least about 2 mm. of mercury at 20° C. The term "nonvolatile" means that the oil has a vapor pressure of less than about 2 mm. of mercury at 20° C.

A. Volatile Oils

Suitable volatile oils generally have a viscosity ranging from about 0.5 to 200,000 centistokes 25° C. and include linear silicones, cyclic silicones, paraffinic hydrocarbons, or mixtures thereof.

1. Volatile Silicones

Cyclic silicones are one type of volatile silicone that may be used in the composition. Such silicones have the general formula:

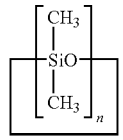

where n=3-6, preferably 4, 5, or 6.

Also suitable are linear volatile silicones, for example, those having the general formula:

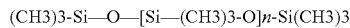

where n=0, 1, 2, 3, 4, or 5, preferably 0, 1, 2, 3, or 4.

Cyclic and linear volatile silicones are available from various commercial sources including Dow Corning Corporation and General Electric. The Dow Corning linear volatile silicones are sold under the tradenames Dow Corning 244, 245, 344, and 200 fluids. These fluids include hexamethyldisiloxane (viscosity 0.65 centistokes (abbreviated cst)), octamethyltrisiloxane (1.0 cst), decamethyltetrasiloxane (1.5 cst), dodecamethylpentasiloxane (2 cst) and mixtures thereof, with all viscosity measurements being at 25° C.

Suitable branched volatile silicones include alkyl trimethicones such as methyl trimethicone, a branched volatile silicone having the general formula:

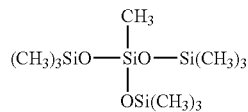

Methyl trimethicone may be purchased from Shin-Etsu Silicones under the tradename TMF-1.5, having a viscosity of 1.5 centistokes at 25° C.

2. Volatile Paraffinic Hydrocarbons

Also suitable as the volatile oils are various straight or branched chain paraffinic hydrocarbons having 5, 6, 7, 8, 9, 10, 11, 12, 13, 14, 15, 16, 17, 18, 19, or 20 carbon atoms, more preferably 8 to 16 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference. Preferred volatile paraffinic hydrocarbons have a molecular weight of 70-225, preferably 160 to 190 and a boiling point range of 30 to 320, preferably 60 to 260° C., and a viscosity of less than about 10 cst. at 25° C. Such paraffinic hydrocarbons are available from EXXON under the ISOPARS trademark, and from the Permethyl Corporation. Suitable $C_{12}$ isoparaffins are manufactured by Permethyl Corporation under the tradename Permethyl 99A. Various $C_{16}$ isoparaffins commercially available, such as isohexadecane (having the tradename Permethyl R), are also suitable.

B. Non-Volatile Oils

A variety of nonvolatile oils are also suitable for use in the compositions of the invention. The nonvolatile oils generally have a viscosity of greater than about 5 to 10 centistokes at 25° C., and may range in viscosity up to about 1,000,000 centipoise at 25° C. Examples of nonvolatile oils include, but are not limited to:

1. Esters

Suitable esters are mono-, di-, and triesters. The composition may comprise one or more esters selected from the group, or mixtures thereof.

(a) Monoesters

Monoesters are defined as esters formed by the reaction of a monocarboxylic acid having the formula R—COOH, wherein R is a straight or branched chain saturated or unsaturated alkyl having 2 to 45 carbon atoms, or phenyl; and an alcohol having the formula R—OH wherein R is a straight or branched chain saturated or unsaturated alkyl having 2-30 carbon atoms, or phenyl. Both the alcohol and the acid may be substituted with one or more hydroxyl groups. Either one or both of the acid or alcohol may be a "fatty" acid or alcohol, and may have from about 6 to 30 carbon atoms, more preferably 12, 14, 16, 18, or 22 carbon atoms in straight or branched chain, saturated or unsaturated form. Examples of monoester oils that may be used in the compositions of the invention include hexyl laurate, butyl isostearate, hexadecyl isostearate, cetyl palmitate, isostearyl neopentanoate, stearyl heptanoate, isostearyl isononanoate, stearyl lactate, stearyl octanoate, stearyl stearate, isononyl isononanoate, and so on.

(b). Diesters

Suitable diesters are the reaction product of a dicarboxylic acid and an aliphatic or aromatic alcohol or an aliphatic or aromatic alcohol having at least two substituted hydroxyl groups and a monocarboxylic acid. The dicarboxylic acid may contain from 2 to 30 carbon atoms, and may be in the straight or branched chain, saturated or unsaturated form. The dicarboxylic acid may be substituted with one or more hydroxyl groups. The aliphatic or aromatic alcohol may also contain 2 to 30 carbon atoms, and may be in the straight or branched chain, saturated, or unsaturated form. Preferably, one or more of the acid or alcohol is a fatty acid or alcohol, i.e. contains 12-22 carbon atoms. The dicarboxylic acid may also be an alpha hydroxy acid. The ester may be in the dimer or trimer form. Examples of diester oils that may be used in the compositions of the invention include diisotearyl malate, neopentyl glycol dioctanoate, dibutyl sebacate, dicetearyl dimer dilinoleate, dicetyl adipate, diisocetyl adipate, diisononyl adipate, diisostearyl dimer dilinoleate, diisostearyl fumarate, diisostearyl malate, dioctyl malate, and so on.

(c). Triesters

Suitable triesters comprise the reaction product of a tricarboxylic acid and an aliphatic or aromatic alcohol or alternatively the reaction product of an aliphatic or aromatic alcohol having three or more substituted hydroxyl groups with a monocarboxylic acid. As with the mono- and diesters mentioned above, the acid and alcohol contain 2 to 30 carbon atoms, and may be saturated or unsaturated, straight or branched chain, and may be substituted with one or more hydroxyl groups. Preferably, one or more of the acid or alcohol is a fatty acid or alcohol containing 12 to 22 carbon atoms. Examples of triesters include esters of arachidonic, citric, or behenic acids, such as triarachidin, tributyl citrate, triisostearyl citrate, tri $C_{12-13}$ alkyl citrate, tricaprylin, tricaprylyl citrate, tridecyl behenate, trioctyldodecyl citrate, tridecyl behenate; or tridecyl cocoate, tridecyl isononanoate, and so on.

Esters suitable for use in the composition are further described in the C.T.F.A. Cosmetic Ingredient Dictionary and Handbook, Eleventh Edition, 2006, under the classification of "Esters", the text of which is hereby incorporated by reference in its entirety.

2. Hydrocarbon Oils

It may be desirable to incorporate one or more nonvolatile hydrocarbon oils into the composition. Suitable nonvolatile hydrocarbon oils include paraffinic hydrocarbons and olefins, preferably those having greater than about 20 carbon atoms. Examples of such hydrocarbon oils include $C_{24-28}$ olefins, $C_{30-45}$ olefins, $C_{20-40}$ isoparaffins, hydrogenated polyisobutene, polyisobutene, polydecene, hydrogenated polydecene, mineral oil, pentahydrosqualene, squalene, squalane, and mixtures thereof. In one preferred embodiment such hydrocarbons have a molecular weight ranging from about 300 to 1000 Daltons.

3. Glyceryl Esters of Fatty Acids

Synthetic or naturally occurring glyceryl esters of fatty acids, or triglycerides, are also suitable for use in the compositions. Both vegetable and animal sources may be used. Examples of such oils include castor oil, lanolin oil, $C_{10-18}$ triglycerides, caprylic/capric/triglycerides, sweet almond oil, apricot kernel oil, sesame oil, *camelina sativa* oil, tamanu seed oil, coconut oil, corn oil, cottonseed oil, linseed oil, ink oil, olive oil, palm oil, illipe butter, rapeseed oil, soybean oil, grapeseed oil, sunflower seed oil, walnut oil, sunflower seed oil, jojoba seed oil, meadowfoam seed oil, canola oil, murumuru seed butter, and the like.

Also suitable are synthetic or semi-synthetic glyceryl esters, such as fatty acid mono-, di-, and triglycerides which are natural fats or oils that have been modified, for example, mono-, di- or triesters of polyols such as glycerin. In an example, a fatty ($C_{12-22}$) carboxylic acid is reacted with one or more repeating glyceryl groups. glyceryl stearate, diglyceryl diisostearate, polyglyceryl-3 isostearate, polyglyceryl-4 isostearate, polyglyceryl-6 ricinoleate, glyceryl dioleate, glyceryl diisoteate, glyceryl tetraisostearate, glyceryl trioctanoate, diglyceryl distearate, glyceryl linoleate, glyceryl myristate, glyceryl isostearate, PEG castor oils, PEG glyceryl oleates, PEG glyceryl stearates, PEG glyceryl tallowates, and so on.

4. Nonvolatile Silicones

Nonvolatile silicone oils, both water soluble and water insoluble, are also suitable for use in the composition. Such silicones preferably have a viscosity ranging from about greater than 5 to 800,000 cst, preferably 20 to 200,000 cst at 25° C. Suitable water insoluble silicones include amine functional silicones such as amodimethicone.

For example, such nonvolatile silicones may have the following general formula:

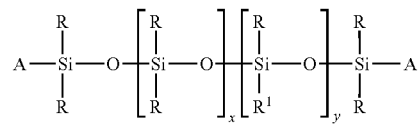

wherein R and R' are each independently $C_{1-30}$ straight or branched chain, saturated or unsaturated alkyl, phenyl or aryl, trialkylsiloxy, and x and y are each independently 1-1,000,000; with the proviso that there is at least one of either x or y, and A is alkyl siloxy endcap unit. Preferred is where A is a methyl siloxy endcap unit; in particular trimethylsiloxy, and R and R' are each independently a $C_{1-30}$ straight or branched chain alkyl, phenyl, or trimethylsiloxy, more preferably a $C_{1-22}$ alkyl, phenyl, or trimethylsiloxy, most preferably methyl, phenyl, or trimethylsiloxy, and resulting silicone is dimethicone, phenyl dimethicone, diphenyl dimethicone, phenyl trimethicone, or trimethylsiloxyphenyl dimethicone. Other examples include alkyl dimethicones such as cetyl dimethicone, and the like wherein at least one R is a fatty alkyl ($C_{12}$, $C_{14}$, $C_{16}$, $C_{18}$, $C_{20}$, or $C_{22}$), and the other R is methyl, and A is a trimethylsiloxy endcap unit, provided such alkyl dimethicone is a pourable liquid at room temperature. Phenyl trimethicone can be purchased from Dow Corning Corporation under the tradename 556 Fluid. Trimethylsiloxyphenyl dimethicone can be purchased from Wacker-Chemie under the tradename PDM-1000. Cetyl dimethicone, also referred to as a liquid silicone wax, may be purchased from Dow Corning as Fluid 2502, or from DeGussa Care & Surface Specialties under the trade names Abil Wax 9801, or 9814.

It may also be desirable to include one or more humectants in the composition. Examples of suitable humectants include glycols, sugars, and the like. Suitable glycols are in monomeric or polymeric form and include polyethylene and polypropylene glycols such as PEG 4-200, which are polyethylene glycols having from 4 to 200 repeating ethylene oxide units; as well as $C_{1-6}$ alkylene glycols such as propylene glycol, butylene glycol, pentylene glycol, and the like. Suitable sugars, some of which are also polyhydric alcohols, are also suitable humectants. Examples of such sugars include glucose, fructose, honey, hydrogenated honey, inositol, maltose, mannitol, maltitol, sorbitol, sucrose, xylitol, xylose, and so on. Also suitable is urea. Preferably, the humectant used in the compositions of the invention is glycerin. Additional surfactants suitable for use in the compositions of the present invention are anionic, cationic, nonionic, amphoteric, or zwitterionic. The composition may contain more than one surfactant. Generally the amount of the surfactant may preferably range from about 0.001-50%, preferably about 0.005-45%, more preferably about 0.01-40% by weight of the total composition. The surfactants include those set forth below.

1. Nonionic Surfactants

A variety of nonionic surface active agents may be used in the claimed compositions. Preferably, such surface active agents HLB (hydrophile/lipophile balance) of about 12-20, more preferably about 13-16. Nonlimiting examples of nonionic surfactants include:

(a). Alkoxylated Alcohols

Suitable alkoxylated alcohols include ethers formed from the reaction of an aliphatic, aromatic, or heterocyclic alcohol with an alkylene oxide, generally ethylene or propylene oxide. Preferably, the alcohol is an aliphatic alcohol, more preferably a fatty alcohol having 10-22 carbon atoms; and the alkylene oxide is ethylene oxide. Examples of preferred alkoxylated alcohols include steareth, ceteth, ceteareth, beheneth, and the like, having from 1 to 200 repeating ethylene oxide units, as well as PEG derivatives of fatty acids such as PEG dioleate, PEG distearate, PEG isostearate, and so on.

(b). Sorbitan Derivatives

Suitable sorbitan derivatives are esters or ethers or sorbitan, which is a heterocyclic ether formed by the dehydration of sorbitol. Sorbitan may be derivatized by ethoxylation and/or esterification of the hydroxyl groups. Suitable acids used for esterification include $C_{1-30}$ acids, more preferably, fatty acids having 6-22 carbon atoms. Examples of suitable sorbitan derivatives include PEG derivatives of sorbitan wherein the number of repeating ethylene oxide units ranges from 2 to 200, such as PEG sorbitan beeswax, glyceryl/sorbitol/oleate/hydroxystearate, PEG sorbitan cocoate, PEG sorbitan diisostearate, PEG sorbitan isostearate, PEG sorbitan lanolate, PEG sorbitan laurate, PEG sorbitan oleate, PEG sorbitan palmitate, PEG sorbitan perisostearate, PEG sorbitan peroleate, PEG sorbitan stearate, PEG sorbitan tetraoleate, PEG sorbitan tetrastearate, PEG sorbitan triisostearate; Polysorbates such as Polysorbate 20-85, Polysorbate 80 acetate; and sorbitan esters such as sorbitan caprylate, cocoate, diisostearate, dioleate, distearate, isostearate, laurate, oleate, olivate, palmitate, sesquiisostearate, sesquioleate, sesquistearate, stearate, triisostearate, trioleate and the like.

(c). Glyceryl Ethers

Also suitable are linear or branched ethers of polyglycerol having the general formula:

$$R-(Gly)_n-OH$$

wherein n is 1-10 and R is a straight or branched, saturated or unsaturated alkyl having 6 to 30 carbon atoms, and Gly is the glycerol residue. Examples of suitable polyglyceryl derivatives include polyglyceryl decaoleates, polyglyceryl caprates, polyglyceryl diisostearates, polyglyceryl distearates, polyglyceryl isopalmitates, polyglyceryl laurates, and the like.

(d). Dialkyl Sulfoxides

Also suitable are long chain dialkyl sulfoxides containing one short chain alkyl or hydroxy alkyl radical of from about 1 to 3 carbon atoms and one long hydrophobic chain which may be an alkyl, alkenyl, hydroxyalkyl, or ketoalkyl radical containing from about 8 to 20 carbon atoms, from 0 to 10 ethylene oxide moieties, and 0 or 1 glyceryl moiety.

(e). Polyethylene Oxide Condensates of Alkyl Phenols

Suitable condensates include the condensation products of alkyl phenols having an alkyl group of 6 to 20 carbon atoms with ethylene oxide being present in amounts of about 10 to 60 moles of ethylene oxide per mole of alkyl phenol.

(f). Condensation Product of Ethylene Diamine

Examples of suitable condensation products of ethylene diamine include products of ethylene oxide with the reaction product of propylene oxide and ethylene diamine.

(g). Long Chain Tertiary Amine Oxides

Preferred long chain tertiary amine oxides include those corresponding to the general formula:

$$R_1R_2R_3NO$$

wherein $R_1$ contains an alkyl, alkenyl or monohydroxyalkyl radical ranging from about 8 to 18 carbon atoms in length, from 0 to about 10 ethylene oxide moieties, and from 0 to about 1 glyceryl moiety and R2 and R3 are each alkyl or monohydroxyalkyl groups containing from about 1 to about 3 carbon atoms.

(h). Long Chain Tertiary Phosphine Oxides

Suitable long chain tertiary phosphine oxides include those corresponding to the general formula:

$$R_1R_2R_3PO$$

wherein $R_1$ contains an alkyl, alkenyl, or monohydroxyalkyl radical having 8 to 18 carbon atoms, from 0-10 ethylene oxide moieties and 0 or 1 glyceryl moiety, and $R_2$ and $R_3$ are each alkyl or monohydroxyalkyl group containing from about 1 to 3 carbon atoms.

(i). Polyhydroxyl Fatty Acid Amides

Examples of $C_{10-18}$ is alkyl($C_{1-6}$)polyhydroxy fatty acid amides such as $C_{12-18}$ methylglucamides, N-alkoxy polyhydroxy fatty acid amides, N-propyl through N-hexyl $C_{12-18}$ glucamides and so on.

(j). Alkyl Polysaccharides

Suitable nonionic surfactants are alkyl polysaccharides, or alkyl glycosides, disclosed in U.S. Pat. Nos. 5,716,418 and 5,756,079, both of which are hereby incorporated by reference. These alkyl glycosides have the general formula:

$$R_1-O-(R_2O)_t-(G)_n-H$$

wherein $R_1$ is a linear or branched alkyl or alkenyl radical having 12 to 30 carbon atoms, $R_2$ is a $C_{2-4}$ alkylene, (G) is an anhydroglucose unit, t is a number between 0 and 10, preferably 0 to 4, and n is a number from about 1 to 15. Examples of such alkyl polysaccharides are octyl, nonydecyl, undecyldodecyl, tridecyl, tetradecyl, pentadecyl, hexadecyl, heptadecyl, and octadecyl, di-, tri-, tetra-, penta-, and hexaglucosides, galactosides, lactosides, glucoses, fructosides, fructoses, and so on. Certain polyglycosides having the above formula are sold by Henkel Corporation under the tradenames APG 300, APG 350, APG 500, APG 550, APG 625, or the tradename Planteren, e.g. Planteren 300, 600, 1200, 2000, and so on.

2. Anionic Surfactants

Also suitable for use in the compositions of the invention are one or more anionic surfactants.

(a). Alkyl Sulfates

Anionic surfactants include alkyl and alkyl ether sulfates generally having the formula $ROSO_3M$ and $RO(C_2H_4O)_xSO_3M$ wherein R is alkyl or alkenyl of from about 10 to 20 carbon atoms, x is 1 to about 10 and M is a water soluble cation such as ammonium, sodium, potassium, or triethanolamine cation.

Another type of anionic surfactant which may be used in the compositions of the invention are water soluble salts of organic, sulfuric acid reaction products of the general formula:

$$R_1SO_3-M$$

wherein $R_1$ is chosen from the group consisting of a straight or branched chain, saturated aliphatic hydrocarbon radical having from about 8 to about 24 carbon atoms, preferably 12 to about 18 carbon atoms; and M is a cation. Examples of such anionic surfactants are salts of organic sulfuric acid reaction products of hydrocarbons such as n-paraffins having 8 to 24 carbon atoms, and a sulfonating agent, such as sulfur trioxide.

(b). Fatty Acids Esterified with Isethionic Acid

Also suitable as anionic surfactants are reaction products of fatty acids esterified with isethionic acid and neutralized with sodium hydroxide. The fatty acids may be derived from coconut oil or other similar vegetable or animal derived oils that contain fatty acids.

(c). Succinates or Succinimates

In addition, succinate and succinimates are suitable anionic surfactants. This class includes compounds such as disodium N-octadecylsulfosuccinate; tetrasodium N-(1,2-dicarboxyethyl)-N-octadecylsulfosuccinate; and esters of sodium sulfosuccinic acid e.g. the dihexyl ester of sodium sulfosuccinic acid, the dioctyl ester of sodium sulfosuccinic acid, and the like.

(d). Olefin Sulfonates

Other suitable anionic surfactants include olefin sulfonates having about 12 to 24 carbon atoms. The term "olefin sulfonate" means a compound that can be produced by sulfonation of an alpha olefin by means of uncomplexed sulfur trioxide, followed by neutralization of the acid reaction mixture in conditions such that any sulfones which have been formed in the reaction are hydrolyzed to give the corresponding hydroxy-alkanesulfonates. The alpha-olefin from which the olefin sulfonate is derived is a mono-olefin having about 12 to 24 carbon atoms, preferably about 14 to 16 carbon atoms.

(e). Soaps

Other suitable anionic surfactants are the beta-alkoxy alkane sulfonates or water soluble soaps thereof such as the salts of $C_{10-20}$ fatty acids, for example coconut and tallow based soaps. Preferred salts are ammonium, potassium, and sodium salts. Soaps may also form through the reaction of one or more fatty acids with mono-, di-, or trialkanolamines.

(f). N-acyl Amino Acids

Still another class of anionic surfactants include N-acyl amino acid surfactants and salts thereof (alkali, alkaline earth, and ammonium salts) having the formula: wherein $R_1$ is a $C_{8-24}$ alkyl or alkenyl radical, preferably $C_{10-18}$; $R_2$ is H, $C_{1-4}$ alkyl, phenyl, or —$CH_2COOM$; $R_3$ is $CX_2$— or $C_{1-2}$ alkoxy, wherein each X independently is H or a $C_{1-6}$ alkyl or alkylester, n is from 1 to 4, and M is H or a salt forming cation as described above. Examples of such surfactants are the N-acyl sarcosinates, including lauroyl sarcosinate, myristoyl sarcosinate, cocoyl sarcosinate, and oleoyl sarcosinate, preferably in sodium or potassium forms.

3. Cationic, Amphoteric, or Zwitterionic Surfactants

Certain types of amphoteric, zwitterionic, or cationic surfactants may also be used as the amphiphilic surface active material. Descriptions of such surfactants are set forth in U.S. Pat. No. 5,843,193, which is hereby incorporated by reference in its entirety.

Amphoteric surfactants that may be used in the compositions of the invention are generally described as derivatives of aliphatic secondary or tertiary amines wherein one aliphatic radical is a straight or branched chain alkyl of 8 to 18 carbon atoms and the other aliphatic radical contains an anionic group such as carboxy, sulfonate, sulfate, phosphate, or phosphonate.

Suitable amphoteric surfactants may be imidazolinium compounds having the general formula:

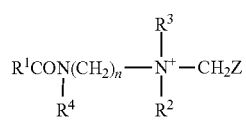

wherein $R_1$ is $C_{8-22}$ alkyl or alkenyl, preferably $C_{12-16}$; $R_2$ is hydrogen or $CH_2CO_2M$, $R_3$ $CH_2CH_2OH$ or $CH_2CH_2OCH_2CHCOOM$; $R_4$ is hydrogen, $CH_2CH_2OH$, or $CH_2CH_2OCH_2CH_2COOM$, Z is $CO_2M$ or $CH_2CO_2M$, n is 2 or 3, preferably 2, M is hydrogen or a cation such as an alkali metal, alkaline earth metal, ammonium, or alkanol ammonium cation. Examples of such materials are marketed under the tradename MIRANOL, by Miranol, Inc.

Also suitable amphoteric surfactants are monocarboxylates or dicarboxylates such as cocoamphocarboxypropionate, cocoamphocarboxypropionic acid, cocoamphocarboxyglycinate, and cocoamphoacetate.

Other types of amphoteric surfactants include aminoalkanoates of the formula R—$NH(CH_2)_nCOOM$ or iminodialkanoates of the formula: R—$N[(CH_2)_mCOOM]_2$ and mixtures thereof, wherein n and m are 1 to 4, R is $C_{8-22}$ alkyl or alkenyl, and M is hydrogen, alkali metal, alkaline earth metal, ammonium or alkanolammonium. Examples of such amphoteric surfactants include n-alkylaminopropionates and n-alkyliminodipropionates, which are sold under the trade name MIRATAINE by Miranol, Inc. or DERIPHAT by Henkel, for example N-lauryl-beta-amino propionic acid, N-lauryl-beta-imino-dipropionic acid, or mixtures thereof.

Zwitterionic surfactants are also suitable for use in the compositions of the invention. The general formula for such surfactants is:

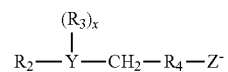

wherein $R_2$ contains an alkyl, alkenyl or hydroxy alkyl radical of from about 8 to about 18 carbon atoms, from 0 to about 10 ethylene oxide moieties and 0 or 1 glyceryl moiety; Y is selected from the group consisting of nitrogen, phosphorus, and sulfur atoms; $R_3$ is an alkyl or monohydroxyalkyl group containing about 1 to 3 carbon atoms; X is 1 when Y is a sulfur atom, and 2 when Y is a nitrogen or phosphorus atom; R4 is an alkylene or hydroxyalkylene of from about 1 to about 4 carbon atoms, and Z is a radical selected from the group consisting of carboxylate, sulfonate, sulfate, phosphonate, and phosphate groups.

Zwitterionic surfactants include betaines, for example higher alkyl betaines such as coco dimethyl carboxymethyl betaine, lauryl dimethyl carboxymethyl betaine, lauryl dimethyl alphacarboxyethyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gamma-carboxylethyl betaine, and mixtures thereof. Also suitable are sulfo- and amido-betaines such as coco dimethyl sulfopropyl betaine, stearyl dimethyl sulfopropyl betaine, babassuamidopropyl betaine, cocamidopropyl betaine, and the like.

The invention will be described further by reference to the following non-limiting examples.

EXAMPLES

Example 1

Test Method to Identify Potentially Moisturizing Ingredient Compositions Introduction Tensile testing has long been used to evaluate the mechanical properties of human hair. The effects of various ingredient compositions (Table II) on the moisture content of human hair were analyzed. Increasing the moisture content of keratin fibers has been shown to decrease Young's modulus, tensile strength and work to break, while increasing extension. Hair was treated with either a control formulation (aqueous carrier only as described in the section entitled "Composition") or an ingredient composition. Cross sectional area of the hair was determined using a Mitutoyo Laser Micrometer. Hair was then stretched to break point on a Dia-Stron MTT675 automated miniature tensile tester and stress/strain curves were created. The resulting curves were then used to evaluate the effects of the ingredient compositions on the mechanical properties of human hair.

Stress/strain curves of human hair have three distinct regions: the Hookean region, yield region and post yield region. In the Hookean region, stress is approximately linear to strain. It is from the slope that the Young's modulus or elastic modulus can be calculated. Young's modulus is defined as follows:

$$E = \Delta F * L / \Delta L * A$$

where $\Delta F$ is the change in force induced by a change in length, $\Delta L$ is the equilibrium length of the fiber, and A is the cross sectional area. The greater the moisture content of the hair tested, the less work is needed to extend the hair because it is softer.

In addition to Young's modulus and cross sectional area, other parameters analyzed include the work to extend the hair to 15% extension, stress to break (also called tensile strength or break load), percentage extension to break and total work to break (the area under the stress/strain curve). It is noted that wet hair is less strong and therefore less force is required to break it (reduced break load). Moisturized hair also breaks more easily as a result of the retention of water.

The testing conducted to evaluate the effects of the moisturizing ingredient compositions is divided into three parts: Part I was conducted to find a composition of ingredients that would effectively deliver moisture to human hair (Table III), Part II was conducted to find a cellulosic polymer that would deliver an additional moisture benefit to the hair (Table Va). In Part III of testing the longevity of the moisturizing affected afforded to the hair by the Ultra Moisturizing Complex was assessed.

Preparation of Test Hair

Evidence suggests that tensile properties of hair are chiefly cortex properties; therefore, to magnify the effects of the ingredient compositions the hair used for testing was damaged to increase its porosity (i.e. separate the scales of the cuticle). It was theorized that an increase in hair porosity should allow for the ingredient compositions to reach the cortex more readily thus magnifying the results of the tensile testing (as compared to testing on undamaged hair).

A 75 mm wide wax-bound tress of standard brown European hair was chemically damaged using a commercial bleach and perm. The hair tress was first bleached using a commercial bleach for 30 minutes at 37° C. The hair swatch was then rinsed for 1 minute with 37° C. tap water. Following bleaching, the hair swatch was treated with a commercial alkaline perm solution which contains 9% sodium thioglycolate. Dwell time for the perm solution was 8 minutes after which the tress was rinsed for 10 minutes with 37° C. tap water. The tress was then allowed to air-neutralize for 10 minutes and then treated with a commercial neutralizer. The tress was processed for an additional 5 minutes. After processing the tress was rinsed for 5 minutes with 37° C. tap water and allowed to air dry.

Preparation of Aqueous Carrier

The aqueous based carrier used for testing consisted of a formulation containing 2.0% Cetyl alcohols, 2.0% Glyceryl Stearate/PEG-100, 2.0% Glycerin, and 0.3% Diazolidinyl Urea. The aqueous carrier also served as the control formulation for the tensile testing.

Preparation of Ingredient Compositions

For each ingredient composition (Tables II, Vb, and VII), the materials were combined in a beaker of appropriate size and heated to 80° C. while being stirred with moderate agitation to ensure a uniform batch. The heat was then turned off and the solution was allowed to return to room temperature while be stirred with moderate agitation.

Treating Hair

For each test conducted (Tables III, VI and IX), two tresses of approximately 7 mm were cut from the larger tress which had been chemically damaged in the procedure above. The tresses were labeled tress 1 and tress 2. A control formulation (aqueous carrier only) was applied to tress 1. The control treatment was applied in excess to tress 1 to ensure saturation. The tress was combed with a plastic comb, placed in a plastic weigh boat and put in an oven at 50° C. for 30 minutes. After removal from the oven, the tress was rinsed for one minute with 37° C. tap water and then allowed to air dry overnight. Next, the assigned ingredient composition was applied in excess to tress 2 to ensure saturation. The tress was combed with a plastic comb, placed in a plastic weigh boat and put in an oven at 50° C. for 30 minutes. After removal from the oven, the tress was rinsed for one minute with 37° C. tap water and then allowed to air dry overnight.

For longevity testing (Table IX), hair was first treated as outlined above. Next, shampoo was applied as follows: shampoo was applied in excess to wet tresses to ensure saturation, the shampoo was then massaged into the tress for 30 seconds then rinsed for 1 minute with 37° C. tap water and then allowed to air dry. This procedure was then repeated nine times for a total of ten washes.

For tresses treated with 5% sodium lauryl sulfate (Table IX), hair was dunked into a beaker containing the sodium lauryl sulfate solution 30 times (1 dunk per second) and then rinsed for 1 minute with 37 C tap water and then allowed to air dry. This procedure was then repeated nine times for a total of ten washes. Tensile testing was conducted after five washes and again after ten washes.

Tensile Testing Procedure

Fifty strands of hair were randomly selected from tress 1 (treated with control) and hand-threaded; root to tip, through brass fasteners. The fasteners were then secured using a press. The samples were labeled 1-50. Fifty strands of hair were randomly selected from tress 2 (treated with assigned ingredient composition) and hand-threaded; root to tip through brass fasteners. The fasteners were then secured using a press. The samples from tress 2 were labeled 51-100. Next, the cross sectional areas of the samples (1-100) were measured with the Laser Scan Micrometer (18m-6100 and LSM 500H) MTT 765. Five slices (scans) were taken of each sample to determine the mean cross-sectional area. The cross sectional area of the hair was later incorporated into the tensile testing data.

Next, samples were then placed in the 100 sample cassette of the Tensile Tester MTT 675 (675.04.02.001). Samples were loaded with their root end towards the inside of the cassette. The samples were than placed in an electro-tech systems, inc. Controlled Environment Chamber Model 518 at 65% relative humidity overnight to equalize. The hair fibers were then extended to the break point at a rate of extension of 12.5 mm/min.

Data was then analyzed using UvWin software and exported to Microsoft Excel for further analysis. Statistical significance of all tests were determined using a two-tailed t-test ($\alpha=0.05$).

The procedure outlined above was repeated for each tensile test as outlined in Table III.

Example 2

Tensile Test Results Part I

Values shown in Table IV represent % change from the water-only control, calculated as: (sample−control)/control× 100.

Test 1

In test 1 (Table III), hair treated with a control formulation was compared to hair treated with Ingredient Composition A (Table II). No significant difference in cross sectional area or total work was found between the control and the hair treated with Ingredient Composition A. Additionally, work at 15% extension, break load and Young's modulus increased significantly while break extension decreased. Results of test 1 are shown in Table IV. These results were not indicative of an increase in keratin moisture content; therefore it was decided to not proceed with further testing of Ingredient Composition A.

Test 2

In test 2 (Table III), hair treated with a control formulation was compared to hair treated with Ingredient Composition B (Table II). No significant difference in cross sectional area, Young's modulus, work at 15% extension, break extension or total work was found when comparing the control to the hair treated with Ingredient Composition B. Break load increased significantly. Results for test 2 are shown in Table IV. These results were not indicative of an increase in keratin moisture content; therefore it was decided to not proceed with further testing of Ingredient Composition B.

Test 3

In test 3 (Table III), hair treated with a control formulation was compared to hair treated with Ingredient Composition C (Table II). No significant difference in cross sectional area, break extension, work at 15% extension or total work was found between the control and the hair treated with Ingredient Composition C. Break load and Young's modulus increased significantly. Results for test 3 are shown in Table IV. These results were not indicative of an increase in keratin moisture content; therefore it was decided to not proceed with further testing of Ingredient Composition C.

Test 4

In test 4 (Table III), hair treated with a control formulation was compared to hair treated with Ingredient Composition D (Table II). No significant difference in cross sectional area, work at 15% extension, break extension or total work was found between the control and the hair treated with Ingredient Composition D. Break load and Young's modulus increased significantly. Results for test 4 are shown in Table IV. These results were not indicative of an increase in keratin moisture content; therefore it was decided to not proceed with further testing of Ingredient Composition D.

Test 5

In test 5 (Table III) hair treated with a control formulation was compared to hair treated with Ingredient Composition E (Table II). No significant difference was found in work at 15% extension, work at, break extension or total work when comparing the control to the hair treated with Ingredient Composition E. Cross sectional area increased significantly while Young's modulus and break load decreased significantly. Results for test 5 are shown in Table IV. Although these results could be indicative of moisturizing properties, due to problems obtaining consistent samples of barley (*Hordeum* distichon) and tomato (*Solanum Lycopersicum*) fruit/leaf/stem extract complex, it was decided to pursue other potential Ingredient Compositions.

Test 6

In test 6 (Table III), hair treated with a control formulation was compared to hair treated with Ingredient Composition F (Table II). No significant difference was found in cross section area, work at 15% extension or total work when comparing the control to the hair treated with Ingredient Composition F. Break load and Young's modulus increased significantly while break extension decreased significantly. Results for test 6 are shown in Table IV. These results were not indicative of an increase in keratin moisture content; therefore it was decided to not proceed with further testing of Ingredient Composition F.

Test 7

In test 7 (Table III), hair treated with a control formulation was compared to hair treated with Ingredient Composition G (Table II). No significant difference was found in cross section area, work at 15% extension, break extension, break load, Young's modulus, or total work when comparing the control to the hair treated with Ingredient Composition G. Results for test 7 are shown in Table IV. These results were not indicative of an increase in keratin moisture content; therefore it was decided to not proceed with further testing of Ingredient Composition G.

Test 8

For test 8 (Table III), hair treated with a control formulation was compared to hair treated with Ingredient Composition H (Table II). No significant difference was found for cross sectional area, work at 15% extension, break extension, break load or total work when comparing the control to the hair treated with Ingredient Composition H. However, Young's modulus decreased significantly, indicating that Ingredient Composition H has moisturizing properties. Results for test 8 are shown in Table IV. Therefore, it was decided to conduct further testing on Composition H.

TABLE II

Potentially moisturizing ingredient compositions

| Ingredient Composition | Description | Weight % |
|---|---|---|
| A | Buriti oil, | 0.5 |
|  | Tahini butter (sesame seed butter) | 0.5 |
|  | Cationic quaternary ammonium (40% active) | 1 |
|  | Aqueous carrier | q.s.* |
| B | Buriti oil, | 0.5 |
|  | Cupuacu butter (*Theobroma grandiflorum* seed butter) | 0.5 |
|  | Cationic quaternary ammonium (40% active) | 1 |
|  | Aqueous carrier | q.s.* |
| C | Buriti oil, | 0.5 |
|  | Cupuacu butter (*Theobroma grandiflorum* seed butter) | 0.5 |
|  | Cationic quaternary ammonium (40% active) | 1 |
|  | Aqueous carrier | q.s.* |
| D | Buriti oil, | 0.5 |
|  | MuruMuru Butter (*Astrocaryum murumur* butter) | 0.5 |
|  | Cationic quaternary ammonium (40% active) | 1 |
|  | Aqueous carrier | q.s.* |
| E | Buriti oil, | 0.5 |
|  | Barley (*Hordeum distichon*) and tomato (Solanum lycopersicum) fruit/leaf/stem extract complex | 0.5 |
|  | Cationic quaternary ammonium (40% active) | 1 |
|  | Aqueous carrier | q.s.* |
| F | Buriti oil, | 0.5 |
|  | Cariocar brasilience fruit oil | 0.5 |
|  | Cationic quaternary ammonium (40% active) | 1 |
|  | Aqueous carrier | q.s.* |
| G | Buriti oil | 0.5 |
|  | Lactobacillus/Eriodictyon californicum Ferment Extract | 0.5 |
|  | Cationic quaternary ammonium (40% active) | 1 |
|  | Aqueous carrier | q.s.* |
| H | Buriti oil, | 0.5 |
|  | Pomegranate Sterols | 0.5 |
|  | Cationic quaternary ammonium (40% active) | 1 |
|  | Aqueous carrier | q.s.* |

*q.s.—quantity sufficient for the total formula weight percentage to equal 100%.

TABLE III

Determination of a moisturizing ingredient composition

| Tensile Test | Description | Treatments tested |
|---|---|---|
| 1 | Dry tensile test (65% RH) | Control vs. Ingredient Composition A |
| 2 | Dry tensile test (65% RH) | Control vs. Ingredient Composition B |
| 3 | Dry tensile test (65% RH) | Control vs. Ingredient Composition C |
| 4 | Dry tensile test (65% RH) | Control vs. Ingredient Composition D |
| 5 | Dry tensile test (65% RH) | Control vs. Ingredient Composition E |
| 6 | Dry tensile test (65% RH) | Control vs. Ingredient Composition F |
| 7 | Dry tensile test (65% RH) | Control vs. Ingredient Composition G |
| 8 | Dry tensile test (65% RH) | Control vs. Ingredient Composition H |

TABLE IV

TENSILE TESTING RESULTS - PART I

| Test No. | Tensile Test | Cross Sectional Area | Work at 15% Extension | Young's Modulus | Break Extension | Break Load | Total Work |
|---|---|---|---|---|---|---|---|
| 1 | | −1.426321007 | 14.01540934 | 15.5849868 | −5.907415465 | 12.50317 | 2.797778 |
| 2 | | −0.59615973 | −0.478742591 | 3.857489992 | 0.637463467 | 5.4259765 | 2.614387 |
| 3 | | −4.294966574 | 10.67904806 | 17.90465535 | −2.262705447 | 10.165952 | 5.317955 |
| 4 | | −0.687644975 | 9.46342141 | 9.108902011 | −2.162673404 | 10.985692 | 8.012582 |
| 5 | | 17.34121661 | 13.99883875 | −21.1319657 | −1.56669523 | −10.566974 | 8.730697 |
| 6 | | −10.42885442 | −0.422245665 | 13.82451969 | −6.44750448 | 10.009663 | −8.156465 |
| 7 | | 4.666817167 | −0.394074298 | −13.02094768 | 1.456873195 | −0.7242837 | 0.162409 |
| 8 | | 2.782649692 | −2.288070503 | −13.02094768 | 1.456873195 | −0.7242837 | 0.162409 |

Example 3

Tensile Testing Results Part II

Values shown in Table VIII represent % change from the water-only control, calculated as: (sample−control)/control× 100.

Test 9

In test 9 (Table Vb), hair treated with a control formulation was compared to hair treated with 0.75% Jaguar C135 cellulosic polymer (Table Va). No significant difference was found in cross section area, work at 15% extension or total work when comparing the control to the hair treated with Jaguar C135 cellulosic polymer. Break load and Young's modulus increased significantly while break extension decreased significantly. The results for test 9 are shown in Table VIII. These results were not indicative of an increase in keratin moisture content; therefore it was decided to not proceed with further testing of Jaguar C135 cellulosic polymer.

Test 10

In test 10 (Table Vb), hair treated with a control formulation was compared to hair treated with 0.75% JR-30M cellulosic polymer (Table Va). No significant difference was found in cross section area when comparing the control to the hair treated with JR-30M cellulosic polymer. There was a significant increase in break extension and significant decrease in break load, Young's modulus, total work and work at 15% extension. The results for test 10 are shown in Table VIII. As a significant decrease in Young's modulus indicates that JR-30M cellulosic polymer may have moisturizing properties, it was decided to conduct further testing with this cellulosic polymer.

Test 11

In Test 11 (Tables VI, VII), an Ultra Moisturizing Complex was created by combining Ingredient Composition H, which was indicated as having moisturizing properties in test 8, with the cellulosic polymer JR30M, which was indicated as having moisturizing properties in test 10. Hair treated with a control formulation was compared to hair treated with this Ultra Moisturizing Complex. No significant difference was found for cross sectional area, work at 15% extension, and break extension, break load or total work when comparing the control to the hair treated with the Ultra Moisturizing Complex). Young's modulus decreased significantly. Results for test 11 are shown in Table VIII. As a significant decrease in Young's modulus is indicative of moisturizing properties attributable to the Ultra Moisturizing Complex, it was decided to conduct further testing to determine the longevity of the moisturizing effect afforded to the hair by the Ultra Moisturizing Complex.

TABLE Va

Potentially moisturizing cellulosic polymers.

| Description | Weight % |
|---|---|
| Cellulosic polymer: Jaguar C135 | 0.75 |
| Aqueous carrier | q.s.* |
| Cellulosic polymer: JR30M | 0.75 |
| Aqueous carrier | q.s.* |

*q.s.—quantity sufficient for the total formula weight percentage to equal 100%.

TABLE Vb

Determination of moisturizing efficacy of cellulosic polymers

| Tensile Test | Description | Treatments tested |
|---|---|---|
| 9 | Dry tensile test (65% RH) | Control vs. Cellulosic polymer: Jaguar C135 |
| 10 | Dry tensile test (65% RH) | Control vs. Cellulosic polymer: JR30M |

TABLE VI

Development of Ultra Moisturizing Ingredient Composition

| Tensile Test | Description | Treatment Tested |
|---|---|---|
| 11 | Dry tensile test (65% RH) | Control vs. Ingredient Composition H with the addition of cellulosic polymer |

TABLE VII

Ultra Moisturizing Complex.

| Ingredient Composition | Description | Weight % |
|---|---|---|
| H | Buriti oil, | 0.5 |
| | Pomegranate Sterols | 0.5 |
| | Cationic quaternary ammonium (40% active) | 1 |
| | cellulosic polymer | 0.75 |
| | Aqueous carrier | q.s.* |

*q.s.—quantity sufficient for the total formula weight percentage to equal 100%.

TABLE VIII

TENSILE TESTING RESULTS - PART II

| Test No. | Tensile Test | Cross Sectional Area | Work at 15% Extension | Young's Modulus | Break Extension | Break Load | Total Work |
|---|---|---|---|---|---|---|---|
| 9 | | 2.474042397 | 11.53887838 | 11.88509808 | −4.436908371 | 7.4770586 | 3.900605 |
| 10 | | 2.521321527 | −62.1000808 | −57.32260732 | 5.090402004 | −21.809942 | −37.70101 |
| 11 | | 2.782649692 | −2.288070503 | −13.02094768 | 1.456873195 | −0.7242837 | 0.162409 |

Example 4

Tensile Test Results Part III

Values shown in Table X represent % change from the water-only control, calculated as: (sample−control)/control× 100.

Test 12 and 13

For test 12 and 13 (Table IX), the longevity of the moisturizing effect afforded to the hair by the Ultra Moisturizing Complex (Table VII) was assessed. In this test, three samples were analyzed: (1) hair treated with a control formulation, (2) hair treated with the Ultra Moisturizing Complex and (3) hair treated with the Ultra Moisturizing Complex and then shampooed ten times with a basic retail shampoo (Prell Shampoo for All Hair Types). The purpose of these tests is to show that the Ultra Moisturizing Complex can provide extended moisturization to the hair; that is, moisture that will last through multiple washes with a standard shampoo.

No significant difference was found for work at 15% extension, total work or break extension when comparing the control to the hair treated with the Ultra Moisturizing Complex and washed ten times with a standard shampoo. Young's modulus and break load decreased significantly while cross sectional area decreased significantly. These results indicate that after ten shampoos with a standard shampoo the moisture afforded to the hair by Ultra Moisturizing Complex still lingers. Test results for test 12 are shown in Table X.

The hair treated with the Ultra Moisture Complex and washed ten times with a basic shampoo was then compared to hair treated with the Ultra Moisture Complex alone to show that the effects of the Ultra Moisture Complex were not significantly diminished after ten shampoos. No significant difference was found for work at 15% extension, total work, break load, Young's modulus or break extension when comparing the control to the hair treated with the Ultra Moisturizing Complex and washed ten times with a standard shampoo. Cross sectional area increased significantly indicating that the multiple shampoos may have caused the hair to swell. Test results for test 13 are shown in Table X.

Test 14

In test 14 (Table IX), the longevity of the moisturizing effect afforded to the hair by the Ultra Moisture Complex (Table VII) was assessed. In this test, hair was treated with a control formulation and compared to hair treated with the Ultra Moisturizing Complex and then shampooed ten times with a 5% solution of sodium lauryl sulfate. The purpose of these tests is to observe whether the Ultra Moisturizing Complex can provide impart moisture to the hair which will last through multiple shampoos. However sodium lauryl sulfate could be considered "harsher" than a typically daily-use shampoo.

No significant difference was found for cross sectional area, work at 15% extension, break load, total work or Young's modulus when comparing the control to the hair treated with the Ultra Moisturizing Complex and washed ten times with a 5% sodium lauryl sulfate. Break extension decrease significantly. These results indicate that after 10 shampoos with 5% sodium lauryl sulfate the moisture afforded to the hair by Ultra Moisturizing Complex does not linger. It was therefore decided to reduce the number of sodium lauryl sulfate washes from ten to five and repeat the testing. Results for test 14 are shown in Table X.

Test 15

In test 15 (Table IX), the longevity of the moisturizing effect afforded to the hair by the Ultra Moisture Complex (Table VII) was assessed. In this test, hair was treated with a control formulation and compared to hair which was treated with the Ultra Moisturizing Complex and then shampooed five times with a 5% solution of sodium lauryl sulfate. The purpose of this test is to observe whether the Ultra Moisturizing Complex can provide moisture to the hair that will last through multiple shampoos.

No significant difference was found for cross sectional area, work at 15% extension, break load, total work or break extension when comparing the control to the hair treated with the Ultra Moisturizing Complex and washed five times with a 5% sodium lauryl sulfate. Young's modulus decreased significantly. These results indicate that after five shampoos with 5% sodium lauryl sulfate the moisture afforded to the hair by Ultra Moisturizing Complex lingers which indicates extending moisturizing properties. Results for test 15 are shown in Table X.

TABLE IX

Longevity testing of the moisturizing effect of Ultra Moisturizing Complex

| Tensile Test | Description | Treatment Tested |
|---|---|---|
| 12 | Dry tensile test (65% RH) | Control vs. Treated with Ultra Moisture Complex then washed 10 times with standard shampoo |
| 13 | Dry tensile test (65% RH) | Ultra Moisture Complex vs. Treated with Ultra Moisture Complex then washed 10 times with standard shampoo. |
| 14 | Dry tensile test (65% RH) | Control vs. Ultra Moisture Complex, then washed 10 times with sodium lauryl sulfate. |
| 15 | Dry tensile test (65% RH) | Control vs. Ultra Moisture Complex, then washed 5 times with sodium lauryl sulfate. |

TABLE X

TENSILE TESTING RESULTS - PART III

| Test No. | Tensile Analysis | Cross Sectional Area | Work at 15% Extension | Young's Modulus | Break Extension | Break Load | Total Work |
|---|---|---|---|---|---|---|---|
| 12 | | 16.47064707 | −2.541959004 | −17.19723399 | 1.314212146 | −8.5148394 | 0.490632 |
| 13 | | 11.15980959 | 3.12843483 | −3.800060545 | 0.354060997 | −0.8060353 | 7.14193 |
| 14 | | 5.225551529 | −0.860368664 | −7.828411334 | −5.290439054 | −1.4825678 | −6.826635 |
| 15 | | 5.802631961 | 9.266803901 | −6.836625219 | −1.001609333 | −0.0046791 | 4.523222 |

TABLE XI

Ultra Moisturizing Complex shampoo composition
The following illustrates a composition of the invention.
Percentages are by weight unless otherwise indicated.

| Phase | | % |
|---|---|---|
| A | Water | 42.2400 |
| A | Tapioca Starch | 0.4500 |
| A | Polyquaternium-10 | 0.7500 |
| A | Glycerin | 5.4200 |
| B | Sodium Methyl Cocoyl Taurate | 8.3700 |
| B | Sodium Cocoyl Isethionate | 23.0000 |
| B | Babassuamidopropyl Betaine | 3.0000 |
| B | Stearamidopropyl Dimethylamine | 2.0000 |
| B | Stearic Acid | 5.0000 |
| B | Sodium Chloride | 2.1200 |
| C | Phenoxyethanol | 0.9500 |
| C | Sodium Gluconate | 0.1000 |
| C | Potassium Sorbate | 0.4500 |
| C | Dimethicone | 2.5000 |
| C | Palmamidopropyl Trimonium Methosulfate | 0.4000 |
| C | *Punica Granatum* (Pomegranate) Sterols | 0.5000 |
| C | *Mauritia Flexuosa* (Buriti) Fruit Oil | 0.5000 |
| C | *Hordeum Distichon* (Barley) Extract | 0.0095 |
| C | *Solanum Lycopersicum* (Tomato) Fruit/Leaf/Stem Extract | 0.0005 |
| C | Citric Acid | 0.1600 |
| C | Fragrance | 0.6000 |
| C | *Astrocaryum Murumuru* Seed Butter | 0.0700 |
| C | *Orbignyz Speciosa* Kernel Oil | 0.4100 |
| C | Ethyl Macadamiate | 1.0000 |

Procedure: Combine Phase A ingredients in the main tank at 25 C while mixing. When uniform, begin heating to 85 C. Add Phase B ingredients one by one when the batch reaches 85 C. Mix for 30 min and begin cooling to 27 C. When batch reaches 45 C, add Phase C ingredients individually while mixing.

TABLE XII

Ultra Moisturizing Complex conditioner composition
The following illustrates a composition of the invention.
Percentages are by weight unless otherwise indicated.

| Phase | | % |
|---|---|---|
| A | Water | 74.6900 |
| A | Sodium Gluconate | 0.2000 |
| A | Tapioca Starch | 0.3600 |
| A | Polyquaternium-10 | 0.7500 |
| A | Glycerin | 2.4200 |
| A | Palmamidopropyl Trimonium Methosulfate | 0.4000 |
| B | Cetearyl Alcohol | 3.5200 |
| B | Cetyl Alcohol | 3.0000 |
| B | Stearyl Alcohol | 1.3000 |
| B | Behentrimonium Methosulfate | 0.9100 |
| B | Stearalkonium Chloride | 2.1300 |
| B | Behenamidopropyltrimonium Methosulfate | 0.6000 |
| B | Babassuamidopropyltrimonium Methosulfate | 0.1000 |
| B | Glyceryl Caprylate | 0.5000 |
| B | Canola Oil | 0.8500 |
| B | Silica | 0.1000 |
| B | Corn (*Zea Mays*) Starch | 0.0500 |
| B | *Limanthes Alba* (Meadowfoam) Seed Oil | 0.5000 |
| B | Tricaprylyl Citrate | 0.0800 |
| C | *Punica Granatum* (Pomegranate) Sterols | 0.5000 |
| C | *Hordeum Distichon* (Barley) Extract | 0.0095 |
| C | *Solanum Lycopersicum* (Tomato) Fruit/Leaf/Stem Extract | 0.0005 |
| C | *Astrocaryum Murumuru* Seed Butter | 0.0700 |
| C | *Orbignya Speciosa* Kernel Oil | 0.4100 |
| C | Dimethicone | 3.3750 |
| C | Ethyl Macadamiate | 0.5000 |

TABLE XII-continued

Ultra Moisturizing Complex conditioner composition
The following illustrates a composition of the invention.
Percentages are by weight unless otherwise indicated.

| Phase | | % |
|---|---|---|
| C | *Maurita Flexuosa* (Buriti) Fruit Oil | 0.5000 |
| C | Cyclopentasiloxane | 2.1250 |
| C | Fragrance | 0.5500 |

Procedure: Add Phase A ingredients to main tank at 25 C, mix until homogenous and begin heating to 82 C. In a separate vessel, add Phase B ingredients and begin heating to 82 C while mixing. When both phases are at 82 C, add Phase B to Phase A and mix for 30 min. Begin cooling to 27 C. When batch reaches 45 C, add Phase C ingredients one by one, while mixing.

TABLE XIII

Ultra Moisturizing Complex treatment masque composition
The following illustrates a composition of the invention.
Percentages are by weight unless otherwise indicated.

| Phase | | % |
|---|---|---|
| A | Water | 57.4300 |
| A | Potassium Sorbate | 0.1000 |
| A | Sodium Gluconate | 0.2000 |
| A | Polyquaternium-10 | 0.7500 |
| A | Glycerin | 2.4200 |
| A | Vinegar | 0.5000 |
| A | Palmamidopropyl Trimonium Methosulfate | 0.4000 |
| A | Cetrimonium Chloride | 0.5800 |
| A | Citric Acid | 0.0200 |
| B | Cetearyl Alcohol | 7.2100 |
| B | Cetyl Alcohol | 3.0000 |
| B | Behentrimonium Methosulfate | 1.0400 |
| B | Behentrimonium Chloride | 0.7500 |
| B | Stearyl Alcohol | 1.3000 |
| B | Behenamidopropyltrimonium Methosulfate | 0.6000 |
| B | Babassuamidopropyltrimonium Methosulfate | 0.1000 |
| B | Stearalkonium Chloride | 3.4000 |
| B | *Astrocaryum Murumuru* Butter | 0.0100 |
| B | Glyceryl Caprylate | 0.5000 |
| B | *Helianthus Annus* (Sunflower) Seed Oil | 0.2500 |
| B | *Simmondsia Chirensis* (Jojoba) Seed Oil | 0.2500 |
| B | *Limnanthes Alba* (Meadowfoam) Seed Oil | 0.2500 |
| B | *Glycine Soya* (Soybean) Oil | 0.2500 |
| B | Tricaprylyl Citrate | 0.5000 |
| B | Dicaprylyl Maleate | 0.5000 |
| B | Distearyldimonium Chloride | 0.7500 |
| B | Dimethiconol Meadowfoamate | 0.5000 |
| C | *Punica Granatum* (Pomegranate) Sterols | 0.5000 |
| C | *Astrocaryum Murumuru* Seed Butter | 0.0700 |
| C | *Orbignya Speciosa* Kernel Oil | 0.4100 |
| C | Dimethicone | 8.7500 |
| C | Ethyl Macadamiate | 0.7500 |
| C | *Mauritia Flexuosa* (Buriti) Friut Oil | 0.5000 |
| C | Dimethiconol Meadowfoamate | 0.5800 |
| C | Cyclopentasiloxane | 4.1700 |
| C | Tocopherol | 0.0100 |
| C | Fragrance | 0.7000 |

Procedure: Add Phase A ingredients to main tank at 25 C, mix until homogenous and begin heating to 80 C. In a separate vessel, add Phase B ingredients and begin heating to 80 C while mixing. When both phases are at 80 C, add Phase B to Phase A and mix for 30 min. Begin cooling to 27 C. When batch reaches 45 C, add Phase C ingredients one by one, while mixing.

Example 8

Ultra Moisturizing Complex Shampoo Tensile and Dimensional Analysis

The purpose of this study was to explore the effects of the Ultra Moisturizing Shampoo on the tensile and dimensional properties of human hair.

Procedure

Part I: Tensile Analysis

Damaging Hair

The effects of the Ultra Moisturizing Complex shampoo were evaluated using level 2 mixed source hair. To induce chemical damage the hair was bleached and permed. The bleach was prepared by weighing 40 volume peroxide developer and hair bleaching powder into a hair color bowl in a 2:1 ratio. The bleach mixture was blended thoroughly with a hair color brush and applied in excess to the hair using the fanning method. After the hair was coated completely and evenly with the bleach, it was set in weigh boats and placed in a 37° C. oven for 30 minutes. Once the hair had processed for 30 minutes, it was rinsed with 37° C. tap water for 1 minute and washed with 5% SLS to remove any excess bleach. Following this procedure, the hair was treated with permanent wave solution alkaline perm solution which contains 9% sodium thioglycolate. The perm solution was left on the hair to process for 8 minutes and then rinsed out for 10 minutes with 37° C. tap water. The hair was allowed to air-neutralize for 10 minutes and then treated with the permanent wave peroxide neutralizer. The neutralizer was left on the hair for 5 minutes at room temperature in accordance with package instructions. After processing the tresses were rinsed for 5 minutes with 37° C. tap water and allowed to air dry.

Treating the Hair

Three tresses of damaged level 2 mixed source hair were assigned the following treatments:

Tress 1: Water only—control
Tress 2: Ultra Moisturizing Complex shampoo (Example V; Table XI)
Tress 3: Sap Moss Asia shampoo*

*Sap Moss Asia shampoo ingredients are as follows: Aqueous (Water, Aqua Purificata, Purified) Extracts: Cetraria Islandica (Iceland Moss) Extract, Yucca Filamentosa (Yucca) Extract, *Saponaria Officinalis* (Soapwort) Extract, *Quillaja Saponaria* Extract, Sodium Cocoyl Isethionate, Sodium Coco-Sulfate, Cetyl Alcohol, Sodium Methyl Cocoyl Taurate, Hydrogenated Castor Oil, Stearamidopropyl Dimethylamine, Galactoarabinan, Olibanum, *Ferula Galbaniflua* (Galbanum) Resin Oil, Babassuamidopropyl Betaine, Lauramidopropyl Betaine, Hydroxypropyl Methylcellulose, Polyquaternium-10, Polyquaternium-7, Fragrance (Parfum), Sodium Chloride, Citric Acid, Sodium Gluconate, Methylchloroisothiazolinone, Methylisothiazolinone, Caramel color.

Tress 1 was rinsed with tap water, massaged for 30 seconds then rinsed with 37° C. tap water for 1 minute. This was done to ensure that all three tresses received equal water exposure and mechanical manipulation. Tress 2 was rinsed with tap water, saturated with the Ultra Moisturizing Complex shampoo, massaged for 30 seconds then rinsed with 37° C. tap water for 1 minute. Tress 3 was rinsed with tap water, saturated with the Sap Moss Asia shampoo, massaged for 30 seconds then rinsed with 37° C. tap water for 1 minute. All three tresses were then allowed to air dry.

Tensile Analysis at 65% Relative Humidity

Fifty strands of hair were randomly selected from tress 1, tress 2, and tress 3 and were hand-threaded; root to tip, through brass crimps. The crimps were then secured using a crimping press and were measured with the laser scan micrometer. Five sets of dimensions were collected from each sample to determine the mean cross sectional area. After collecting dimensional data from the samples, the crimps were loaded with their root end towards the center of the tensile tester 100 slot cassette. The cassette with the crimps was then placed in the controlled environment chamber at 65% relative humidity overnight to equalize. The tensile parameters of the crimps were then measured with the tensile tester. Data was normalized to include the cross sectional area of the hair as determined from the laser scan micrometer and also examined prior to normalization when necessary. The tensile data was then analyzed using UvWin software and exported to Microsoft Excel for further analysis. Statistical significance of all comparisons were determined using a two-tailed t-test ($\alpha$=0.05).

Tensile Analysis at 65% Relative Humidity Retest

The procedure outlined in "Tensile Analysis at 65% Relative Humidity" was repeated for Tress 1 and Tress 2.

Tensile Analysis at 100% Relative Humidity

The procedure is the same as outlined for 65% Relative Humidity for Tress 1 and Tress 2 except that after the crimps were loaded in the cassette, the samples were covered with reverse osmosis water and allowed to sit for a minimum of 10 minutes to ensure their saturation.

Tensile Analysis at 85% Relative Humidity

The procedure is the same as outlined for 65% Relative Humidity for Tress 1 and Tress 2 except that after the crimps were loaded in the cassette, the cassette with the crimps was placed in the controlled environment chamber at 85% relative humidity overnight to equalize.

Part II: Dimensional Data Analysis

The dimensional data collected with the laser scan micrometer in Part I was compiled for all three tensile analyses. The data was analyzed using UvWin software and exported to Microsoft excel for further analysis. Statistical significance was determined using a two-tailed t-test ($\alpha$=0.05).

Part III: Break Extension Data Analysis

The break extension data collected with the tensile tester in Part I was compiled for all three tensile analyses. The data was analyzed using UvWin software and exported to Microsoft excel for further analysis. Statistical significance was determined using a two-tailed t-test ($\alpha$=0.05).

Results

All the data collected for this study was analyzed using the paired two-tailed t-test in the data analysis tools of Microsoft Excel. The t-tests were performed utilizing the "Two-sample Assuming Equal Variance" option.

Part I: Tensile Analysis

Values shown in Tables XIV-XVI represent % change from the control, calculated as:

(sample−control)/control×100. For all Tables, "sample" refers to the treatment with Ultra Moisturizing Complex. For Tables XIV and XV, "control" means "water-only control".

Tensile Analysis at 65% Relative Humidity

When comparing the water treated control hair to the hair treated with the Ultra Moisturizing Complex shampoo, there was no significant difference in the cross sectional area, Young's modulus, break extension, break load, or total work between the two tresses. Results are shown in Table XIV.

Upon analysis of the retest conducted at 65% relative humidity, there was again no significant difference in cross sectional area, break extension, break load, or total work between the Ultra Moisturizing Complex shampoo treated hair and the control. There was a significant decrease in Young's modulus for the hair treated with the Ultra Moisturizing Complex shampoo.

When comparing the hair treated with the Ultra Moisturizing Complex shampoo to the hair treated with the Sap Moss Asia shampoo, there was no significant difference break extension or total work. There was a significant decrease in Young's modulus for the hair treated with the Ultra Moisturizing Complex shampoo. There was a significant increase in the cross sectional area of the hair for the Buriti Moist treated hair when compared to the hair treated with the Sap Moss Asia shampoo. A significant difference in the cross sectional area prevented the incorporation of the dimensional data into the normalized break load calculation. As a result, the non-normalized break load was calculated. Upon analysis, there was no significant difference in the non-normalized break load between the two treatments. Results are shown in Table XV.

Tensile Analysis at 100% Relative Humidity

When comparing the water treated control hair to the hair treated with the Ultra Moisturizing Complex shampoo, there was no significant difference in the cross sectional area, Young's modulus, break load, or total work between the two tresses. There was a significant increase in break extension for the tress treated with the Ultra Moisturizing Complex shampoo. Results are shown in Table XIV.

Tensile Analysis at 85% Relative Humidity

When comparing the control hair to the hair treated with the Ultra Moisturizing Complex shampoo, there was no significant difference in the cross sectional area, break load, or total work between the two tresses. There was a significant decrease in Young's modulus and a significant increase in break extension for the tress treated with the Ultra Moisturizing Complex shampoo. Results are shown in Table XIV.

Part II: Dimensional Data Analysis

When comparing the complied data from the tensile analyses in Part I for the water treatment control hair to the hair treated with the Ultra Moisturizing Complex shampoo, there was a significant increase in the cross sectional area and diameter for the hair treated with the Ultra Moisturizing Complex shampoo.

In comparison to the Sap Moss Asia shampoo treated hair, there was a significant increase in the cross sectional area for the hair treated with the Ultra Moisturizing Complex shampoo. There was no significant difference in diameter between the two samples. Results are shown in Table XVI.

Part III: Break Extension Data Analysis

When analyzing the compiled break extension data from the 100%, 85%, and 65% relative humidity tensile analyses for the hair treated with the Ultra Moisturizing Complex shampoo and the control hair, there was a significant increase (4.19% change from the control; results not shown) in break extension for the hair treated with the Ultra Moisturizing Complex shampoo.

TABLE XIV

TENSILE ANALYSIS TEST RESULTS:
ULTRA MOISTURIZING COMPLEX SHAMPOO vs. CONTROL

| Treatment | Tensile Analysis | Cross Sectional Area | Young's Modulus | Break Extension | Break Load | Total Work |
|---|---|---|---|---|---|---|
| 65% RH | | 2.63 | −2.97 | −0.63 | −1.84 | −1.99 |
| 65% RH Retest | | 4.42 | −6.55 | 0.73 | −2.05 | 2 |
| 85% RH | | 1.99 | −18.3 | 4.79 | −3.47 | −5.15 |
| 100% RH | | 5.5 | −8.36 | 6.02 | −4.57 | 10.1 |

TABLE XV

TENSILE ANALYSIS TEST RESULTS: ULTRA MOISTURIZING COMPLEX SHAMPOO vs SAP MOSS ASIA SHAMPOO

| Treatment | Tensile Analysis | Cross Sectional Area | Young's Modulus | Break Extension | Non-Normalized Break Load | Total Work |
|---|---|---|---|---|---|---|
| 65% RH | | 34.98 | −29.78 | 0.51 | 6.75 | 6.64 |

TABLE XVI

DIMENSIONAL DATA ANALYSIS

| | ULTRA MOISTURIZING COMPLEX SHAMPOO vs. CONTROL | | ULTRA MOISTURIZING COMPLEX SHAMPOO vs. SAP MOSS ASIA SHAMPOO | |
|---|---|---|---|---|
| | Cross Sectional Area | Diameter | Cross Sectional Area | Diameter |
| Dimensional Test | 4.22 | 1.82 | 5.45 | 2.08 |

Conclusions

Part I: Tensile Analysis

When tested at 65% relative humidity, there was no significant difference in cross sectional area, Young's modulus, break extension, break load, or total work between the hair treated with the Ultra Moisturizing Complex shampoo and the water treated control. This lack of significant difference in any of the parameters indicates that the Ultra Moisturizing Complex shampoo may not affect the tensile properties of human hair. Since previous tensile analysis of the Ultra Moisturizing Complex shampoo indicated moisturization properties, a retest was performed at 65% relative humidity. Upon analysis of the retest results, there was again no significant difference in cross sectional area, break extension, break load, or total work between the samples. There was, however a significant decrease in Young's modulus for the hair treated with the Ultra Moisturizing Complex shampoo in comparison to the untreated control. This decrease in Young's modulus supports previous results and indicates that the Ultra Moisturizing Complex shampoo significantly moisturizes human hair.

When analyzing the results obtained from the 100% relative humidity tensile analysis, there was no significant difference in cross sectional area, Young's modulus, break load, or total work between the Ultra Moisturizing Complex shampoo treated hair and the untreated control. There was a significant increase in the break extension for the hair treated with the Ultra Moisturizing Complex shampoo. An increase in break extension indicates that the elasticity of the hair has increased and if often seen in hair that has been moisturized. To further explore the effects of the Ultra Moisturizing Complex shampoo on the tensile properties of human hair a tensile analysis was conducted at 85% relative humidity.

Tensile analysis conducted at 85% relative humidity is usually done to assess the effects of leave-on products. Although the Ultra Moisturizing Complex shampoo was not applied as a leave on product, collecting tensile data from a third humidity can be helpful in further understanding the effects of a treatment. When analyzing the data, there was no significant difference in cross sectional area, break load, or total work. There was again a significant decrease in Young's modulus and an increase in break extension, further supporting that the hair was moisturized and the elasticity has increased.

To determine how the effects of the Ultra Moisturizing Complex shampoo compare to the effects of Sap Moss Asia shampoo on the mechanical properties of human hair, a tensile analysis was performed at 65% relative humidity. Upon analysis, there was a significant increase in cross sectional area for the hair treated with the Ultra Moisturizing Complex shampoo. An increase in cross sectional area could be attributed to swelling of the hair due to increased moisture content, coating of the cuticle, or unpredicted variances in the hair used for testing. However, since testing has shown that the shampoo moisturizes, in this study the most likely reason for the increase in cross sectional area is swelling of the hair fiber due to an increase in moisture. This significant increase in the cross sectional area prevented the incorporation of the dimensional data into the normalized break load calculation. As a result, the non-normalized break load was calculated. Upon analysis of the results, there was no significant difference in the non-normalized break load between the treatments. There was a significant decrease in Young's modulus for the hair treated with the Ultra Moisturizing Complex, indicating that the hair was moisturized as compared to the hair treated with the Sap Moss Asia shampoo. There was no significant difference in break extension or total work between the two treatments.

Overall, the tensile analysis in this study indicates that the Ultra Moisturizing Complex shampoo significantly moisturizes human hair and also moisturizes hair significantly more that the Sap Moss Asia shampoo formulation. Part II: Dimensional Data Analysis When analyzing the cross sectional area and diameter of the untreated control and the hair treated with the Ultra Moisturizing Complex shampoo, there was a significant increase in cross sectional area by an average of 4.2% and in the diameter of the hair by an average of 1.8% for the hair treated with the Ultra Moisturizing Complex shampoo. An increase in cross sectional area may be due to deposits on the cuticle or swelling of the hair in response to the increased moisture content. Improper calibration or unpredicted variances in the hair strands are less likely responsible for the increase in hair dimensions since the data was combined from three separate tensile analyses, helping to ensure a low variance. It was noted that scanning electron microscopy could be performed to determine whether the Ultra Moisturizing Complex shampoo is depositing on the cuticle. When comparing the Ultra Moisturizing Complex shampoo treated hair to the hair treated with the Sap Moss Asia shampoo collected in Part I, there was an increase in the cross sectional area by an average of 5.5% for the Ultra Moisturizing Complex shampoo treated hair. There was an increase in diameter by an average of 2.2% for the Ultra Moisturizing Complex treated hair; however this increase was not significant.

Overall, the results of the dimensional data analysis indicate that the Ultra Moisturizing Complex shampoo significantly increases the cross sectional area and diameter of human hair. The Ultra Moisturizing Complex shampoo also significantly increases the cross sectional area of the hair more than the Sap Moss Asia shampoo. By increasing the dimensions of the hair fiber, the Ultra Moisturizing Complex shampoo significantly thickens human hair. Part III: Break Extension Data Analysis The break extension data was compiled for all three tensile analyses from Part I and then analyzed. Upon analysis, the break extension for the hair treated with the Ultra Moisturizing Complex shampoo significantly increased by an average of 4.20% when compared to the control. This increase indicates that the Ultra Moisturizing Complex shampoo significantly increases the elasticity of human hair.

Example 9

Ultra Moisturizing Complex Regimen (Shampoo: Example 5 Table XI and Conditioner: Example 6 Table XII)

Tensile Analysis

The purpose of this study was to explore the effects of the Ultra Moisturizing Complex regimen, consisting of the Ultra Moisturizing Complex shampoo and conditioner, on the tensile and dimensional properties of human hair.
Procedure
Damaging Hair The effects of the Ultra Moisturizing Complex regimen were evaluated using level 2 mixed source hair. To induce damage the hair was bleached and permed. The bleach was prepared by weighing out 40 volume peroxide developer and hair bleaching powder into a hair color bowl in a 2:1 ratio. The bleach mixture was blended thoroughly with a hair color brush and applied in excess to the hair using the fanning method. After the hair was coated completely and evenly with the bleach, it was set in weigh boats and placed in a 37° C. oven for 30 minutes. Once the hair had processed for 30 minutes, it was rinsed with 37° C. tap water for 1 minute and washed with Scalp Benefits shampoo (Aveda) to remove any excess bleach. Following this procedure, the hair was treated with permanent wave alkaline perm solution which contains 9% sodium thioglycolate. The perm solution was left on the hair to process for 8 minutes and then rinsed out for 10 minutes with 37° C. tap water. The hair was allowed to air-neutralize for 10 minutes and then treated with the permanent wave neutralizer. The neutralizer was left on the hair for 5 minutes at room temperature in accordance with package instructions. After processing the tresses were rinsed for 5 minutes with 37° C. tap water and allowed to air dry.
Part I: Ultra Moisturizing Complex Regimen Tensile Analysis
Treating Hair Two approximately 7 mm wide tresses of damaged level 2 mixed source hair were assigned the following treatments:
Tress 1: Water only—control
Tress 2: Ultra Moisturizing Complex regimen Tress 1 was rinsed with tap water, massaged for 30 seconds, and then rinsed with 37° C. tap water for 1 minute, massaged for 30 seconds, then rinsed again for 1 minute with 37° C. tap water and allowed to air dry. This was done to ensure that both tresses received equal water exposure and mechanical manipulation. Tress 2 was rinsed with tap water, saturated with the Ultra Moisturizing Complex shampoo, massaged for 30 seconds, and then rinsed with 37° C. tap water for 1 minute. The tress was then saturated with the Ultra Moisturizing Complex conditioner, massaged for 30 seconds, rinsed for 1 minute with 37° C. tap water, and allowed to air dry.
Tensile Analysis at 65% Relative Humidity Fifty strands of hair were randomly selected from each of the tresses and were hand-threaded; root to tip, through brass crimps. The crimps were then secured using a crimping press and were measured with the laser scan micrometer. Five sets of dimensions were collected from each sample to determine the mean cross sectional area. After collecting dimensional data from the samples, the crimps were loaded with their root end towards the center of the tensile tester 100 slot cassette. The cassette with the crimps was then placed in the controlled environment chamber at 65% relative humidity overnight to equalize. The tensile parameters of the crimps were then measured with the tensile tester. Data was normalized to include the cross sectional area of the hair as determined from the laser scan micrometer and also examined prior to normalization when necessary. The tensile data was then analyzed using UvWin software and exported to Microsoft Excel for further analysis. Statistical significance of all comparisons were determined using a two-tailed t-test ($\alpha=0.05$).
Tensile Analysis at 100% Relative Humidity The procedure is the same as outlined for 65% Relative Humidity for Tress 1 and Tress 2 except that after the crimps were loaded in the cassette, the samples were covered with reverse osmosis water and allowed to sit for a minimum of 10 minutes to ensure their saturation.

The samples were then covered with reverse osmosis water and allowed to sit for a minimum of 10 minutes to ensure their saturation.
Tensile Analysis at 85% Relative Humidity The procedure is the same as outlined for 65% Relative Humidity for Tress 1 and Tress 2 except that after the crimps were loaded in the cassette, the cassette with the crimps was placed in the controlled environment chamber at 85% relative humidity overnight to equalize.
Part II: Ultra Moisturizing Complex Regimen vs. Sap Moss Asia Regimen Tensile Analysis
Treating Hair Two approximately 7 mm wide tresses of damaged level 2 mixed source hair were assigned the following treatments:
Tress 1: Sap Moss Asia regimen (shampoo and conditioner**)
Tress 2: Ultra Moisturizing Complex regimen

**Sap Moss Asia conditioner ingredients are as follows: Aqueous (Water, Aqua Purificata, Purified) Extract: Cetraria Islandica (Iceland Moss) Extract, Glycerin, Dipalmitoylethyl Hydroxyethylmonium Methosulfate, Cetearyl Alcohol, Cyclopentasiloxane, Dicaprylyl Ether, Dicetyldimonium Chloride, Galactoarabinan, *Ferula* Galbaniflua (Galbanum) Resin Oil, Olibanum, *Prunus Armeniaca* (Apricot) Kernel Extract, Hydrolyzed Wheat Protein, Wheat Amino Acids, Hydrolyzed Wheat Starch, Panthenol, Glyceryl Stearate, Guar Hydroxypropyltrimonium Chloride, Cetyl Alcohol, Behentrimonium Methosulfate, Cetrimonium Chloride, PEG/PPG-18/18 Dimethicone, Cetyl Hydroxyethylcellulose, Fragrance (Parfum), Magnesium Sulfate, Sodium Gluconate, Potassium Sorbate, Phenoxyethanol, Caramel color.

Tress 1 was rinsed with tap water, saturated with the Sap Moss Asia shampoo, massaged for 30 seconds, and then rinsed with 37° C. tap water for 1 minute. The tress was then saturated with the Sap Moss Asia conditioner, massaged for 30 seconds, rinsed for 1 minute with 37° C. tap water, and allowed to air dry. Tress 2 was rinsed with tap water, saturated with the Ultra Moisturizing Complex shampoo, massaged for 30 seconds, and then rinsed with 37° C. tap water for 1 minute. The tress was then saturated with the Ultra Moisturizing Complex conditioner, massaged for 30 seconds, rinsed for 1 minute with 37° C. tap water, and allowed to air dry.

Tensile Analysis at 65% Relative Humidity

Tensile analysis was performed following the procedure outlined in the "Tensile Analysis at 65% Relative Humidity" section of Part I.

Part III: Dimensional Data Analysis

Dimensional measurements were collected for the hair treated with the Ultra Moisturizing Complex regimen and for the control hair using the laser scan micrometer from the three tensile analyses in Part I. Dimensional measurements were also collected for the hair treated with the Ultra Moisturizing Complex regimen and for the hair treated with the Sap Moss Asia regimen from tensile analysis in Part II. Dimensions were collected and analyzed as described previously. Statistical significance was determined using a two-tailed t-test ($\alpha=0.05$).

Part IV: Break Extension Data Analysis

Break extension measurements were collected for the hair treated with the Ultra Moisturizing Complex regimen and for the control using the tensile tester during the tensile analyses in Part I. Break extension data from all three tensile analyses was compiled and statistical significance was determined using a two-tailed t-test ($\alpha=0.05$).

Results

The data were analyzed using the paired t-test in the Data Analysis tools in Microsoft Excel. The option used for the t-tests in this study was "Two-sample Assuming Equal Variance." A two-tailed t-test was used.

Part I: Ultra Moisturizing Complex Regimen Tensile Analysis

Values shown in Table XVII-XIX represent % change from the control, calculated as:

(sample−control)/control×100. For all Tables, "sample" refers to treatment with the Ultra Moisturizing Complex. For Tables XVII and XIX, "control" refers to "water-only".

Tensile Analysis at 65% Relative Humidity

Testing at 65% relative humidity revealed no significant differences between the control hair and the hair treated with the Ultra Moisturizing Complex regimen for cross sectional area, break extension, or total work. There was a significant decrease in Young's modulus and break load for the hair treated with the Ultra Moisturizing Complex regimen I. Results are shown in Table XVII.

Tensile Analysis at 100% Relative Humidity

When tested at 100% relative humidity, there was no significant difference in cross sectional area, Young's modulus, break extension, or total work between the hair treated with the Ultra Moisturizing Complex regimen I and the control. There was a significant decrease in the break load for the Ultra Moisturizing Complex regimen treated hair. Results are shown in Table XVII.

Tensile Analysis at 85% Relative Humidity

Testing at 85% relative humidity revealed no significant differences between the control hair and the hair treated with the Ultra Moisturizing Complex regimen for cross sectional area or total work. There were significant decreases in Young's modulus and break load for the hair treated with the Ultra Moisturizing Complex regimen. There was also a significant increase in break extension for the treated hair. Results are shown in Table XVII.

Part II: Ultra Moisturizing Complex Regimen vs. Sap Moss Asia Regimen Tensile Analysis Tensile Analysis at 65% Relative Humidity When tested at 65% relative humidity, there was no significant difference in total work between the hair treated with the Ultra Moisturizing Complex regimen and the hair treated with the Sap Moss Asia regimen. There was a significant increase in cross sectional area for the hair treated with the Ultra Moisturizing Complex regimen in comparison to the hair treated with the Sap Moss Asia regimen. Since there was a significant difference in cross sectional area, the dimensional data could not be incorporated into the normalized break load calculation; therefore the non-normalized break load was calculated and analyzed. Upon analysis, there was a significant increase in the non-normalized break load for the Ultra Moisturizing Complex treated hair. There was also a significant decrease in Young's modulus and break extension for the hair treated with the Ultra Moisturizing Complex regimen. Results are shown in Table XVIII.

Part III: Dimensional Data Analysis

When analyzing the compiled dimensional data from the tensile analyses in Part I, there was a significant increase in cross sectional area and diameter for the hair treated with the Ultra Moisturizing Complex regimen in comparison to the control treated hair. When comparing the dimensional data from the hair treated with the Ultra Moisturizing Complex regimen and the hair treated with the Sap Moss Asia regimen from the tensile analysis in Part II, cross sectional area and diameter significantly increased for the Ultra Moisturizing Complex treated hair. Results are shown in Table XIX.

Part IV: Break Extension Data Analysis

When analyzing all of the compiled break extension data from the 65%, 100%, and 85% tensile analyses for the hair treated with the Ultra Moisturizing Complex regimen and the control treated hair from Part I, there was no significant difference in break extension between the treatments.

TABLE XVII

TENSILE ANALYSIS:
ULTRA MOISTURIZING COMPLEX REGIMEN vs CONTROL

| Treatment | Tensile Analysis | Cross Sectional Area | Young's Modulus | Break Extension | Break Load | Total Work |
|---|---|---|---|---|---|---|
| 65% RH | | 7.05 | −18.8 | −1.3 | −4.49 | −1.57 |
| 85% RH | | 7.68 | −17.2 | 6.26 | −11.5 | −5.1 |
| 100% RH | | 9.72 | −8.39 | −1.83 | −10.1 | −0.47 |

TABLE XVIII

TENSILE ANALYSIS TEST RESULTS
ULTRA MOISTURIZING REGIMEN vs
SAP MOSS ASIA REGIMEN

| Treatment | Tensile Test | Cross Sectional Area | Young's Modulus | Break Extension | Break Load | Total Work |
|---|---|---|---|---|---|---|
| 65% RH | | 22.9 | −16 | −4.89 | 22 | 8.35 |

TABLE XIX

DIMENSIONAL DATA ANALYSIS

| | ULTRA MOISTURIZING COMPLEX REGIMEN vs. CONTROL | | ULTRA MOISTURIZING COMPLEX REGIMEN vs. SAP MOSS ASIA REGIMEN | |
|---|---|---|---|---|
| | Cross Sectional Area | Diameter | Cross Sectional Area | Diameter |
| Dimensional Test | 9.93 | 4.8 | 26.3 | 11.2 |

Conclusions

Part I: Ultra Moisturizing Complex Regimen I Tensile Analysis

When tested at 65% relative humidity, there was no significant difference in cross sectional area, break extension, or total work between the Ultra Moisturizing Complex regimen treated hair and the control treated hair. There was a significant decrease in Young's modulus and break load for the hair treated with the Ultra Moisturizing Complex regimen. A decrease in Young's modulus indicates an increase in the moisture content of the hair, and a decrease in break load supports the presence of moisturization properties.

The tensile results from the test at 100% relative humidity revealed no significant difference in cross sectional area, Young's modulus, break extension, or total work between the Ultra Moisturizing Complex regimen treated hair and the control treated hair. There was a significant decrease in break load for the Ultra Moisturizing Complex treated hair. A decrease in break load suggests that less force was needed to break the hair, and is often seen in hair that has been moisturized. To further explore the moisturizing properties of the Ultra Moisturizing Complex regimen, tensile analysis was performed at 85% relative humidity.

Tensile testing at 85% relative humidity is typically used to assess the effects of leave on products. While the Ultra Moisturizing Complex shampoo and conditioner were not applied as leave on treatments, collecting data from a third humidity range can help clarify the effects of a treatment. Upon analysis, there was no significant difference in cross sectional area or total work between the treatments. There was a significant decrease in Young's modulus and break load indicating an increase in moisture, supporting the results of the 65% and 100% relative humidity tensile analyses. There was also a significant increase in break extension indicating an increase in the elasticity of the hair.

Overall, the results of this tensile analysis indicate that the Ultra Moisturizing Complex shampoo and conditioner significantly moisturize human hair. Part II: Ultra Moisturizing Complex Regimen vs. Sap Moss Asia Regimen Tensile Analysis The Ultra Moisturizing Complex shampoo and conditioner were compared to the Sap Moss Asia shampoo and conditioner to determine whether the Ultra Moisturizing Complex regimen is more moisturizing than the Sap Moss Asia regimen. The results from the 65% relative humidity tensile analysis revealed a significant increase in the cross sectional area for the hair treated with the Ultra Moisturizing Complex regimen. It was contemplated that an increase in cross sectional area could be the result of any of human error in the improper calibration of the laser micrometer, swelling of the hair, deposits on the cuticle, or unpredicted variances with the hair used for tensile testing. Significant changes in cross sectional area prevent the incorporation of the dimensional data into the normalized break load calculation; therefore, the non-normalized break load was calculated and analyzed. Upon analysis, there was a significant increase in the non-normalized break load for the hair treated with the Ultra Moisturizing Complex regimen. An increase in break load suggests that more force was needed to break the hair. There was also a significant decrease in Young's modulus and break extension for the hair treated with the Ultra Moisturizing Complex regimen in comparison to the hair treated with the Sap Moss Asia regimen. A decrease in Young's modulus indicates that the moisture content of the hair has increased, and the decrease in break extension indicates that the hair has become less elastic. The decrease in Young's modulus and the increase in break load are in conflict with one another, suggesting both moisturization and strengthening properties. However, for a treatment to strengthen the moisture content of the hair fiber must decrease. Strengthening properties cannot be confirmed at 65% relative humidity and must be assessed under wet conditions which are known to be more sensitive for strength. Further testing in necessary to determine if the Ultra Moisturizing Complex regimen significantly moisturizes hair more than the Sap Moss Asia regimen. Part III: Dimensional Data Analysis To assess the hair dimensions, the individual measurements that were taken with the laser scan micrometer, as opposed to the average of the readings, were analyzed. Upon analysis, there was a significant increase in the cross sectional area by an average of 9.9% and an increase in diameter by an average of 11.2% for the hair treated with the Ultra Moisturizing Complex shampoo and conditioner in comparison to the control. As an increase in hair dimensions could be the result of swelling of the cortex due to an increased moisture content of the hair fiber or deposits on the cuticle, scanning electron microscopy was utilized to determine of the Ultra Moisturizing Complex regimen is depositing on the cuticle.

When comparing the hair treated with the Ultra Moisturizing Complex regimen to the hair treated with the Sap Moss Asia regimen, there was a significant increase in the cross sectional area by an average of 26.3% and an increase in diameter by an average of 11.2% for the treated with the Ultra Moisturizing Complex shampoo and conditioner. These increases indicate that the Ultra Moisturizing Complex regimen increases hair dimensions to a significantly greater degree than does the Sap Moss Asia regimen. Part IV: Break Extension Data Analysis Since the break extension significantly increased when tested at 85% relative humidity, all of the break extension data was compiled for the 65%, 100%, and 85% relative humidity tensile analyses from Part I and then analyzed. Upon analysis, there was an average increase of 0.90% in the elasticity for the hair treated with the Ultra Moisturizing Complex regimen; however this increase in break extension was not significant between the two treatments. This indicates that the Ultra Moisturizing Complex regimen does not significantly affect the elasticity of human hair.

Example 10

Buriti Oil Scanning Electron Microscopy Analysis

The purpose of this study was to explore the effects of buriti oil on the surface morphology of human hair using scanning electron microscopy (SEM).

This study explored the effects of buriti oil on the surface morphology of human hair. The effects of the oil were assessed on level 6 mixed source hair via scanning electron microscopy (SEM).

To determine if the conditioner base caused a visible change in surface morphology of the hair strands, the images (not shown) of the untreated hair were compared to the images (not shown) of the hair treated with the conditioner base. Subjective comparison of these images revealed little difference between the strands aside from a few clumps of conditioner ingredients clinging to the surface of the conditioner treated hair. The cuticle micrograph of the base treated hair shows a clear, well defined cuticle and no visible deposition or coating. This demonstrates that the conditioner base used in this study has very little impact on the appearance of human hair.

Once it had been established that the conditioner base does not impact the surface morphology of human hair strands, it could be assumed that any changes in the appearance of hair treated with buriti oil can be attributed to the oil and not the conditioner base used as the aqueous carrier in this study. To explore the effects of the buriti oil, the SEM images (not shown) collected from hair treated with conditioner base and the hair treated with the buriti oil were compared. Subjective analysis revealed that the surface of the hair treated with buriti oil was coated with a thin, flaky residue. Based on these results, it can be concluded that buriti oil coats human hair. The hair coated with the buriti oil has a thickened appearance.

Example 11

Effects of the Substitution of Ingredients in Ultra Moisturizing Complex Conditioner on the Tensile Properties of Human Hair The purpose of this study was to examine the effects of the Ultra Moisturizing Complex Conditioner in which various ingredients were substituted for the components shown to be effective in moisturizing human hair.

Procedure Part I: Analysis of the Effects of Dry Remedy Conditioner with the Deep Moisture Complex on the Tensile Properties of Human Hair Hair Preparation This test was performed using level 4 mixed source hair. To induce chemical damage the hair was bleached and permed. A commercial bleach was blended thoroughly with a hair color brush and applied in excess to the hair. After the hair was coated completely and evenly with the bleach, it was set in weigh boats and placed in a 37° C. oven for 30 minutes. Once the hair had processed for 30 minutes, it was rinsed thoroughly with 37° C. tap water. The tresses were clamped to a rod suspended 200 mm below the faucet. The water was kept at 37° C.±2° C., and the flow rate was kept at a rate that caused a 400 mL beaker to fill and overflow in 4 to 5 seconds. The tresses were then washed with Scalp Benefits Shampoo* to remove any excess bleach. Following this procedure, the hair was treated with a commercial alkaline perm solution which contains 9% sodium thioglycolate. The perm solution was left on the hair to process for 8 minutes and then rinsed out for 10 minutes with 37° C. tap water following the previously outlined procedure. The hair was allowed to air-neutralize for 10 minutes and then treated with a commercial neutralizer. The neutralizer was left on the hair for 5 minutes at room temperature in accordance with package instructions. After processing the tresses were rinsed for 5 minutes with 37° C. tap water following the previously outlined procedure and allowed to air dry.

* Aveda Scalp Benefits Shampoo ingredients: Aqueous (water, aqua purificata, purified) extracts: *hippophae rhamnoides* extract, *echinacea purpurea* (coneflower) extract, *arctium lappa* (burdock) root extract, *salvia officinalis* (sage) leaf extract, babassuamidopropyl betaine, sodium cocoyl isethionate, sodium methyl cocoyl taurate, sodium chloride, disodium laureth sulfosuccinate, *narcissus tazetta* bulb extract, PEG-12 dimethicone, dimethicone PEG-8 meadowfoamate, fragrance, polysorbate 20, isostearamidopropyl morpholine lactate, citric acid, disodium EDTA, potassium sorbate, methylparaben, methylchloroisothiazolinone, methylisothiazolinone.

Treating the Hair

For the tensile analysis two approximately 7 mm wide tresses of damaged level 4 mixed source hair (Medium Brown Caucasian/European hair from multiple persons) were assigned the following treatments:

Tress 1: No Treatment Control
Tress 2: Ultra Moisturizing Complex Conditioner

Tress 1 was set aside and left untreated. Ultra Moisturizing Complex Conditioner was applied in excess to tress 2. The tress was then massaged for 30 seconds and rinsed with 37° C. tap water for 1 minute using the procedure outlined in the "Hair Preparation" section. The tresses were then allowed to air dry.

Tensile Analysis at 65% Relative Humidity

Fifty strands of hair were randomly selected from each of the swatches and were hand-threaded, root to tip, through brass crimps. The crimps were then secured using a crimping press and were measured with the laser scan micrometer. Five sets of dimensions were collected from each sample to determine the mean cross-sectional area. After collecting dimensional data from the samples, the crimps were loaded with their root end towards the center of the tensile tester 100 slot cassette. The cassette with the crimps was then placed in the controlled environment chamber at 65% relative humidity overnight to equalize. The tensile parameters of the crimps were then measured with the tensile tester. Data was normalized to include the cross sectional area of the hair as determined from the laser scan micrometer and also examined prior to normalization when necessary. The tensile data was then analyzed using UvWin software and exported to Microsoft Excel for further analysis. Statistical significance of the data was determined using a two-tailed t-test (p<0.05).

Part II: Analysis of the Effects of Ultra Moisturizing Complex Conditioner Containing Soybean Oil Instead of Buriti Oil on the Tensile Properties of Human Hair Hair Preparation The tresses used in this portion of the study were chemically damaged using the procedure described in part I.

Treating the Hair

For the tensile analysis two approximately 7 mm wide tresses of damaged level 4 mixed source hair were assigned the following treatments:

Tress 1: No Treatment Control
Tress 2: Ultra Moisturizing Complex Conditioner containing soybean oil instead of buriti oil The tresses were treated following the procedure outlined in the "Treating the Hair" section of part I.

Tensile Analysis at 65% Relative Humidity

Tensile analysis was performed at 65% relative humidity as outlined in part I.

Part III: Analysis of the Effects of Ultra Moisturizing Complex Conditioner Containing Meadowfoam Oil Instead of Buriti Oil on the Tensile Properties of Human Hair Hair Preparation The tresses used in this portion of the study were chemically damaged using the procedure described in part I.

Treating the Hair

For the tensile analysis two approximately 7 mm wide tresses of damaged level 4 mixed source hair were assigned the following treatments:

Tress 1: No Treatment Control
Tress 2: Ultra Moisturizing Complex Conditioner containing meadowfoam oil instead of buriti oil The tresses were treated following the procedure outlined in the "Treating the Hair" section of part I.

Tensile Analysis at 65% Relative Humidity

Tensile analysis was performed at 65% relative humidity as outlined in part I.

Part IV: Analysis of the Effects of Ultra Moisturizing Complex Conditioner Containing Cholesterol Instead of Pomegranate Sterols on the Tensile Properties of Human Hair Hair Preparation The tresses used in this portion of the study were chemically damaged using the procedure described in part I.

Treating the Hair

For the tensile analysis two approximately 7 mm wide tresses of damaged level 4 mixed source hair were assigned the following treatments:

Tress 1: No Treatment Control
Tress 2: Ultra Moisturizing Complex Conditioner containing cholesterols instead of pomegranate sterols The tresses were treated following the procedure outlined in the "Treating the Hair" section of part I.

Tensile Analysis at 65% Relative Humidity

Tensile analysis was performed at 65% relative humidity as outlined in part I.

Results

The data was analyzed using the paired t-test in the Data Analysis tools in Microsoft Excel. The option used for the t-tests in this study was Two-sample Assuming Equal Variance. A two-tailed t-test was used. The values shown in Tables XX, XXI, XXII and XXIII represent the % change from the no treatment control, and are calculated as: (sample−control)/control×100.

Part I: Analysis of the Effects of Ultra Moisturizing Complex Conditioner on the Tensile Properties of Human Hair Tensile Analysis at 65% Relative Humidity Analysis of the 65% relative humidity results no significant differences in cross sectional area, break extension, break load or total work between the treatments (Table XX). There was, however, a significant decrease in Young's modulus for the conditioner treated hair as compared to the untreated control hair (Table XX).

TABLE XX

TENSILE ANALYSIS TEST RESULTS
ULTRA MOISTURIZING COMPLEX vs. CONTROL CONTAINING BURITI OIL

| Treatment | Tensile Test | Cross Sectional Area (sq.microns) | Young's Modulus (Pa) | Break Extension (% strain) | Break Load (gmf/sq.micron) | Total Work (J) |
|---|---|---|---|---|---|---|
| 65% RH | | 9.58 | −9.66 | 3.07 | −1.52 | 9.48 |

Part II: Analysis of the Effects of Ultra Moisturizing Complex Conditioner Containing Soybean Oil Instead of Buriti Oil on the Tensile Properties of Human Hair Tensile Analysis at 65% Relative Humidity Analysis of the 65% relative humidity results revealed no significant differences in cross sectional area, break extension, total work or break load between the treatments (Table XXI). Young's modulus was significantly lower for the conditioner treated hair as compared to the untreated control hair (Table XXI).

TABLE XXI

TENSILE ANALYSIS TEST RESULTS
ULTRA MOISTURIZING COMPLEX CONTAINING
SOYBEAN OIL vs. CONTROL

| Treatment | Tensile Test | Cross Sectional Area (sq.microns) | Young's Modulus (Pa) | Break Extension (% strain) | Break Load (gmf/sq.micron) | Total Work (J) |
|---|---|---|---|---|---|---|
| 65% RH | | 4.93 | −10.2 | 2.42 | −0.05 | 4.37 |

Part III: Analysis of the Effects of Ultra Moisturizing Complex Conditioner Containing Meadowfoam Oil Instead of Buriti Oil on the Tensile Properties of Human Hair Tensile Analysis at 65% Relative Humidity Analysis of the results revealed no significant differences in cross sectional area, break extension, break load or total work between the treatments (Table XXII). There was, however, a significant decrease in Young's modulus for the conditioner treated hair as compared to the untreated control hair (Table XXII).

TABLE XXII

**TENSILE ANALYSIS TEST RESULTS
ULTRA MOISTURIZING COMPLEX CONTAINING
MEADOWFOAM OIL vs. CONTROL**

| Treatment | Tensile Test | Cross Sectional Area (sq.microns) | Young's Modulus (Pa) | Break Extension (% strain) | Break Load (gmf/sq.micron) | Total Work (J) |
|---|---|---|---|---|---|---|
| 65% RH | | 12.23 | −5.22 | −1.51 | −0.21 | 8.59 |

Part IV: Analysis of the Effects of Ultra Moisturizing Complex Conditioner Containing Cholesterol Instead of ABS Pomegranate Sterols on the Tensile Properties of Human Hair Tensile Analysis at 65% Relative Humidity Analysis of the 65% relative humidity results revealed no significant differences in cross sectional area, break extension, total work, break load or Young's modulus (Table XXIII) between the treatments.

TABLE XXIII

**TENSILE ANALYSIS TEST RESULTS
ULTRA MOISTURIZING COMPLEX CONTAINING
CHOLESTEROL vs. CONTROL**

| Treatment | Tensile Test | Cross Sectional Area (sq.microns) | Young's Modulus (Pa) | Break Extension (% strain) | Break Load (gmf/sq.micron) | Total Work (J) |
|---|---|---|---|---|---|---|
| 65% RH | | 2.50 | −3.69 | 1.09 | 0.17 | 1.13 |

Conclusion

This study was conducted to determine the effects of the conditioner on the moisture content of human hair. This study also examined the effects of formulations of the Ultra Moisturizing Complex Conditioner in which various ingredients were substituted for the raw materials typically found in the Ultra Moisturizing Complex Conditioner. Testing was conducted at 65% relative humidity for each formulation. Damaged level 4 mixed source hair was used for all tensile analyses.

Part I: Analysis of the Effects of Ultra Moisturizing Complex Conditioner on the Tensile Properties of Human Hair To determine the effects the Ultra Moisturizing Complex Conditioner has on the moisture content of hair, a tress treated with the conditioner was compared to an untreated control tress. Tensile analysis at 65% relative humidity revealed no significant differences in cross sectional area, break load, break extension or total work between the treatments. There was, however, a significant decrease in Young's modulus for the conditioner treated hair as compared to the untreated control hair. This decrease indicates that the Ultra Moisturizing Complex Conditioner significantly moisturizes human hair.

Overall, the results of part I of this study indicate that the Ultra Moisturizing Complex Conditioner moisturizes human hair.

Part II: Analysis of the Effects of Ultra Moisturizing Complex Conditioner Containing Soybean Oil Instead of Buriti Oil on the Tensile Properties of Human Hair To examine the effects of the Ultra Moisturizing Complex Conditioner containing soybean oil instead of buriti oil on the moisture content of hair, a tress treated with the conditioner was compared to an untreated control tress. At 65% relative humidity, there were no significant differences in cross sectional area, break extension, total work or break load between the treatments. Young's modulus was significantly lower for the conditioner treated hair as compared to the untreated control hair. As discussed previously, a decrease in Young's modulus indicates that the treatment significantly moisturizes human hair.

Overall, the results of part II of this study indicate that the Ultra Moisturizing Complex Conditioner containing soybean oil instead of buriti oil moisturizes human hair.

Part III: Analysis of the Effects of Ultra Moisturizing Complex Conditioner Containing Meadowfoam Oil Instead of Buriti Oil on the Tensile Properties of Human Hair To examine the effects of the Ultra Moisturizing Complex Conditioner containing meadowfoam oil instead of buriti oil on the moisture content of hair, a tress treated with the conditioner was compared to an untreated control tress. At 65% relative humidity, there were no significant differences in cross sectional area, break extension, break load or total work between the treatments. There was, however, a significant decrease in Young's modulus for the conditioner treated hair as compared to the untreated control hair. As discussed in parts I and II, this decrease indicates that treatment with the Ultra Moisturizing Complex Conditioner containing meadowfoam oil instead of buriti oil significantly moisturizes human hair.

Overall, the results of part III of this study indicate that the Ultra Moisturizing Complex Conditioner containing meadowfoam oil instead of buriti oil moisturizes human hair.

Part IV: Analysis of the Effects of Ultra Moisturizing Complex Conditioner Containing Cholesterol Instead of Pomegranate Sterols on the Tensile Properties of Human Hair To examine the effects of the Ultra Moisturizing Complex containing synthetic cholesterol instead of pomegranate sterols on the moisture content of hair, a tress treated with the conditioner was compared to an untreated control tress. At 65% relative humidity, there were no significant differences in cross sectional area, break extension, total work, break load or Young's modulus between the treatments. This lack of significant difference indicates that the Ultra Moisturizing Complex Conditioner containing cholesterol instead of pomegranate sterols does not impact the moisture content of human hair.

Overall, the results of part IV of this study indicate that the Ultra Moisturizing Complex Conditioner containing cholesterol instead of pomegranate sterols does not impact the moisture content of human hair.

In summary, the results of this study indicate that Ultra Moisturizing Complex Conditioner containing soybean oil instead of buriti oil and Ultra Moisturizing Complex Conditioner containing meadowfoam oil instead of buriti oil moisturize human hair while the Ultra Moisturizing Complex Conditioner containing cholesterol instead of pomegranate sterols does not impact the moisture content of human hair.

What we claim is:

1. An aqueous composition for providing extended moisturization to hair, scalp and/or skin, consisting essentially of: a. a cationic component; b. an oil containing about 70% or greater unsaturated fatty acids with chain length of $C_{18}$ or greater; c. a phytosterol; and d. a cellulosic polymer; wherein a, b, c and d are provided in amounts effective to impart moisturization to the hair, scalp and/or skin which lasts through ten washings with a conventional shampoo product.

2. The aqueous moisturizing composition of claim 1, wherein the cationic component, the oil, the phytosterol and the cellulosic polymer are present in the composition in a ratio of about 0.5-1:0.7-1.5:0.7-1.5:1-2.

3. The aqueous moisturizing composition of claim 2, wherein the cationic component, the oil, the phytosterol and the cellulosic polymer are present in the composition in a ratio of about 0.8:1:1:1.5.

4. The aqueous moisturizing composition of claim 1, wherein the cationic component is a cationic quaternary compound.

5. The aqueous moisturizing composition of claim 4, wherein the cationic quaternary compound is a quaternary ammonium salt, a salt of a fatty amine or an amidoamine salt.

6. The aqueous moisturizing composition of claim 5, wherein the quaternary ammonium salt is selected from the group consisting of behenalkonium chloride, behentrimonium chloride, behentrimonium methosulfate, behenamidopropyltrimonium methosulfate, cetalkonium chloride, cetrimonium chloride, cetrimonium methosulfate, dibehenyldimonium methosulfate, dicapryl/dicaprylyl dimonium chloride, babassuamidopropyltrimonium chloride, babassuamido propyl konium chloride, palmamidopropyl trimonium chloride, palmamidopropyl trimonium methosulfate, stearalkonium chloride, distearyldimonium chloride and stearamidopropyl trimonium chloride.

7. The aqueous moisturizing composition of claim 6, wherein the quaternary ammonium salt is palmamidopropyl trimonium chloride or palmamidopropyl trimonium methosulfate.

8. The aqueous moisturizing composition of claim 5, wherein the amidoamine salt is selected from the group consisting of stearamidopropyl dimethylamine, babassuamiodpropyl dimethylamine, and cocamidopropyl dimethylamine.

9. The aqueous moisturizing composition of claim 1, wherein the cationic component is a cationic polymer.

10. The aqueous moisturizing composition of claim 9, wherein the cationic polymer is a copolymer of vinylpyrrolidone, a homopolymer of dimethyldiallylammonium chloride, a copolymer of dimethyldiallylammonium chloride and acrylamide, an acrylic or methacrylic homopolymer or copolymer or a cationic silicone.

11. The aqueous moisturizing composition of claim 1, wherein the oil is selected from the group consisting of buriti oil, soybean oil, meadowfoam oil, safflower oil, sesame oil and canola oil.

12. The aqueous moisturizing composition of claim 11, wherein the oil is buriti oil.

13. The aqueous moisturizing composition of claim 1, wherein the phytosterol comprises one or more of campesterol, sitosterol, stigmasterol and ergosterol.

14. The aqueous moisturizing composition of claim 1, wherein the phytosterol is derived from pomegranate.

15. The aqueous moisturizing composition of claim 1, wherein the cellulosic polymer comprises a film forming alkyl cellulosic polymer, a cationic guar gum derivative or a combination thereof.

16. The aqueous moisturizing composition of claim 15, wherein the film forming alkyl cellulosic polymer is selected from the group consisting of methyl cellulose, ethyl cellulose, hydroxyethyl cellulose, hydroxypropyl methyl cellulose and quaternary ammonium salts thereof.

17. The aqueous moisturizing composition of claim 15, wherein the cellulosic polymer is a natural film forming polymer derived from guar bean, locust bean, starches, carrageenan or xanthan gum.

18. The aqueous moisturizing composition of claim 15, wherein the cellulosic polymer comprises a combination of the film forming alkyl cellulosic polymer and the cationic guar gum derivative.

19. The aqueous moisturizing composition of claim 18, wherein the cellulosic polymer is guar hydroxypropyl imonium chloride.

20. The aqueous moisturizing composition of claim 15, wherein the film forming alkyl cellulosic polymer is a trialkyl ammonium substituted epoxide of an alkyl cellulosic polymer.

21. The aqueous moisturizing composition of claim 20, wherein the trialkyl ammonium substituted epoxide of the alkyl cellulosic polymer is polyquaternium 10.

22. The aqueous moisturizing composition of claim 1, wherein each of the cationic component, the oil, the phytosterol and the cellulosic polymer is present in the composition in an amount in the range of from about 0.05-20% by weight of the total composition.

23. The aqueous moisturizing composition of claim 1, wherein the cationic component is present in the composition in an amount in the range of from about 0.1-10%, the oil is present in the composition in an amount in the range of from about 0.25-2.5%, the phytosterol is present in the composition in an amount in the range of from about 0.25-2.5%, and the cellulosic polymer is present in the range of from about 0.375-3.75%, wherein the amounts are based on the total weight of the composition.

24. The aqueous moisturizing composition of claim 1, which comprises one or more of perfumes, anti-dandruff agents, additional hair conditioning agents, plant extracts, skin conditioning agents, dyes, pearlescent aids, foam boosters, additional surfactants or emulsifiers, nonionic cosurfactants, additional oils, humectants, suspending or thickening or viscosity adjusting agents, pH adjusting agents, preservatives, proteins, skin active agents, sunscreens, and anti-oxidants.

25. The aqueous moisturizing composition of claim 1, which comprises palmamidopropyl trimonium methosulfate, buriti oil, pomegranate phytosterols and polyquaternium 10, each present in the composition in an amount in the range of about 0.05%-20% by weight of the total composition.

26. The aqueous moisturizing composition of claim 1, which is a cleansing, conditioning or treatment product for the scalp, the hair or the skin.

* * * * *